US011136316B2

(12) United States Patent
Spiegel et al.

(10) Patent No.: US 11,136,316 B2
(45) Date of Patent: Oct. 5, 2021

(54) BIFUNCTIONAL MOLECULES WITH ANTIBODY-RECRUITING AND ENTRY INHIBITORY ACTIVITY AGAINST THE HUMAN IMMUNODEFICIENCY VIRUS

(71) Applicant: YALE UNIVERSITY, New Haven, CT (US)

(72) Inventors: David Spiegel, New Haven, CT (US); Christopher Parker, Medina, OH (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 16/894,362

(22) Filed: Jun. 5, 2020

(65) Prior Publication Data

US 2020/0392121 A1 Dec. 17, 2020

Related U.S. Application Data

(62) Division of application No. 16/037,678, filed on Jul. 17, 2018, now Pat. No. 10,703,743, which is a division of application No. 15/379,969, filed on Dec. 15, 2016, now Pat. No. 10,030,008, which is a division of application No. 13/988,251, filed as application No. PCT/US2011/061174 on Nov. 17, 2011, now Pat. No. 9,562,038.

(60) Provisional application No. 61/414,977, filed on Nov. 18, 2010, provisional application No. 61/522,518, filed on Aug. 11, 2011.

(51) Int. Cl.

| | |
|---|---|
| *C07D 405/14* | (2006.01) |
| *A61K 31/496* | (2006.01) |
| *A61K 45/06* | (2006.01) |
| *A61K 9/00* | (2006.01) |

(52) U.S. Cl.
CPC .......... *C07D 405/14* (2013.01); *A61K 9/0014* (2013.01); *A61K 31/496* (2013.01); *A61K 45/06* (2013.01)

(58) Field of Classification Search
CPC .. C07D 405/14; A61K 31/496; A61K 9/0014; A61K 45/06; A61P 31/12
See application file for complete search history.

(56) References Cited

U.S. PATENT DOCUMENTS

| | | | |
|---|---|---|---|
| 4,522,811 | A | 6/1985 | Eppstein et al. |
| 5,608,060 | A | 3/1997 | Axworthy |
| 2003/0069245 | A1 | 4/2003 | Wallace et al. |
| 2003/0216435 | A1 | 11/2003 | Getman |
| 2008/0268462 | A1 | 10/2008 | Kosmeder |

FOREIGN PATENT DOCUMENTS

| | | | |
|---|---|---|---|
| WO | 8910754 | A1 | 11/1989 |
| WO | 0204440 | A1 | 1/2002 |
| WO | 2012019003 | A1 | 2/2002 |
| WO | 2009139863 | A2 | 11/2009 |
| WO | 2010093706 | A1 | 8/2010 |
| WO | 2011/046946 | A2 | 4/2011 |

OTHER PUBLICATIONS

Brekke OH, Sandlie I. Therapeutic Antibodies for Human Diseases at the Dawn of the Twenty-First Century. Nature Review Drug Discovery, 2003;2:52-62.
Allen TM. Ligand-Targeted Therapeutics in Anticancer Therapy. Nat Rev Cancer, 2002;2:750-763.
Klein JS, et al. Examination of the contributions of size and avidity to the neutralization mechanisms of the anti-HIV antibodies b12 and 4E10. Proceedings of the National Academy of Sciences, 2009;Abstract.
Shaw GM, et al. Molecular Characterization of Human T-Cell Leukemia (Lymphotropic Virus Type III) in the Acquired Immune Deficiency Syndrome. Science, 226;1165-1171.
Carlson CB, et al. Selective Tumor Cell Targeting Using Low-Affinity, Multivalent Interactions. ACS Chem Biol, 2007;2:119-127.
Owen RM, et al. Bifunctional Ligands that Target Cells Displaying the alpha-v-beta-3 Integrin. Chem Bio Chem, 2007;8:68-82.
Popkov M, et al. Instant immunity through chemically programmable vaccination and covalent self-assembly. Proc Natl Acad Sci U.S.A, 2009;106:4378-4383.
Popkov M, et al. Small molecule drug activity in melanoma models may be dramatically enhanced with an antibody effector Intl J Cancer, 2006;119:1194-1207.
Low PS, et al. Discovery and Development of Folic-Acid-Based Receptor Targeting for Imaging and Therapy of Cancer and Inflammatory Diseases. Acc Chem Res, 2008;41:120-129.
Lu Y, et al. Folate-Targeted Dinitrophenyl Hapten Immunotherapy: Effect of Linker Chemistry on Antituor Activity and Allergic Potential. Mol Pharm, 2007;4:695-706.
Rader C, et al. Chemically programmed monoclonal antibodies for cancer therapy: Adaptor immunotherapy based on a covalent antibody catalyst. Proc Natl Acad Sci U.S.A, 2003;100:5396-5400.

(Continued)

*Primary Examiner* — Sarah Pihonak
(74) *Attorney, Agent, or Firm* — Henry D. Coleman; R. Neil Sudol

(57) ABSTRACT

The present invention is directed to new bifunctional compounds and methods for treating HIV infections. The bifunctional small molecules, generally referred to as ARM-HI's, function through orthogonal pathways, by inhibiting the gp120-CD4 interaction, and by recruiting anti-DNP antibodies to gp120-expressing cells, thereby preventing cell infection and spread of HIV. It has been shown that ARM-HI's bind to gp120 and gp-120 expressing cells competitively with CD4, thereby decreasing viral infectivity as shown by an MT-2 cell assay, the binding leading to formation of a ternary complex by recruiting anti-DNP antibodies to bind thereto, the antibodies present in the ternary complex promoting the complement-dependent destruction of the gp120-expressing cells. Compounds and methods are described herein.

20 Claims, 6 Drawing Sheets

(56) References Cited

OTHER PUBLICATIONS

Bertozzi CR, Bednarski MD. Antibody Targeting to Bacterial Cells Using Receptor-Specific Ligands. Am Chem Soc, 1992;114:2242-2245.

Li J, et al. Bacteria Targeted by Human Natural Antibodies Using alpha-gal Conjugated Receptor-specific Glycopolymers. Bioorg Med Chem, 1999;7:1549-1558.

Krisfinamurthy VM, et al. Promotion of opsonization by antibodies and phagocytosis of Gram-positive bacteria by a bifunctional polyacrylamide. Biomaterials, 2006;27:3663-3674.

Shokat KM, Schultz PG. Redirecting the Immune Response: Ligand-Mediated Immunogenicity. Am Chem Soc, 1991;113:1861-1862.

Niaicker KP, et al. Design and synthesis of alpha-Gal-conjugated peptide T20 as novel antiviral agent for HIV-immunotargeting. Org Blomol Chem, 2004;2:660-664.

Perdomo MF, et al. Neutralization of HIV-1 by redirection of natural antibodies. Proc Natl Acad Sci U.S.A, 2008;105:8.

Corson TW, et al. Design and Application of Bifunctional Small Molecules: Why Two Heads Are Better Than One. ACS Chem Biol, 2008;3:677-692.

Karjalainen K, Makela O. Concentrations of three hapten-binding immunoglobulins in pooled normal human serum. Eur J Immunol, 1976;6:88-93.

Farah FS. Natural Antibodies Specific to the 2,4-Dinitrophenyl Group. Immunology, 1973;25:217-226.

Ortega E, et al. Natural DNP-Binding Immunoglobulins and Antibody Multispecificity. Mol Immunol, 1984;21:883-888.

Jormalainen S, Makela O. Anti-hapten antibodies in normal sera. Eur J Immunol, 1971;1:471-478.

Miranda LR, et al. Cell surface expression of the HIV-1 envelope glycoproteins is directed from intracellular CTLA-4-containing regulated secretory granules. Proc Natl Acad Sci U.S.A, 2002;99:8031-8036.

Rawool DB, et al. Utilization of FC Receptors as a Mucosal Vaccine Strategy against an Intraceullular Bacterium, Francisella tularensis. Immunol, 2008;180:5548-5557.

Wang J, et al. Modification and structure-activity relationship of a small molecule HIV-1 inhibitor targeting the viral envelope glycoprotein gp120. Org Biomol Chem, 2005;3:1781-1786.

Kong R, et al. Prediction of the binding mode between BMS-378806 and HIV-1 gp120 by docking and molecular dynamics simulation. Biochem Biophys Acta, 2006;1764:766-7728.

Rostovtsev VV, et al. A Stepwise Huisgen Cycloaddition Process: Copper (I)-catalyzed Regioselective "Ligation" of Azides and Terminal Alkynes. Angew Chem., 1nt Ed. 2002;41:2596-2599.

Tornoe CW, et al. Peptidotriazoles on Solid Phase: [1,2,3]-Triazoles by Regiospecific Copper(I)-Catalyzed 1,3-Dipolar Cycloadditions of Terminal Alkynes to Azides. J Org Chem, 2002;67:3057-3064.

Wang T, et al. Discovery of 4-Benzoyl-1[(4-methoxy-1H-pyrrolo[2,3-b]pyridin-3-yl)oxoacetyl]-2-(R)-methylpiperazine (BMS-378806): A Novel HIV-1 Attachment Inhibitor That Interferes with CD4-gp120 Interactions. J Med Chem, 2003;46:4236-4239.

Platt EJ, et al. Effects of CCR5 and CD4 Cell Surface Concentrations on Infections by Macrophagetropic Isolates of Human Immunodeficiency Virus Type 1. J Virol, 1998;72:2855-2864.

Parker CG, et al. An Antibody-Recruiting Small Molecule That Targets HIV gp120. J Am Chem Soc, 2009;131:16392-16394.

CAS STN RN 1070541-85-3, publ. Nov. 4, 2008, Abstract.

Hansch, et al. Immunochemistry, 1978, Pergamon Press Ltd, vol. 15, pp. 535-540.

Parker CG, et al. Supporting Information, An Antibody-Recruiting Small Molecule That Targets HIV gp120. J Am Chem Soc, 2009:S1-S21.

Scheme 1
Synthesis of Compound 2

Scheme 2
Synthesis of Compound 9

Scheme 3
General Chemical Synthetic Route to Additional Analogs

BIFUNCTIONAL MOLECULES WITH ANTIBODY-RECRUITING AND ENTRY INHIBITORY ACTIVITY AGAINST THE HUMAN IMMUNODEFICIENCY VIRUS

PRIORITY CLAIM AND GRANT SUPPORT

This application is a Divisional application of U.S. patent application Ser. No. 16/037,678 filed on Jul. 17, 2018, now U.S. Pat. No. 10,703,343, issued Jul. 7, 2020, which is a Divisional application of United States patent application serial number U.S. Ser. No. 15/379,969, filed Dec. 15, 2016, now U.S. Pat. No. 10,030,008, issued Jul. 24, 2018, which is a Divisional application of U.S. patent application Ser. No. 13/988,251, filed May 17, 2013, now U.S. Pat. No. 9,562,038, issued Feb. 7, 2017, which is a 371 of international patent application number PCT/US2011/061174, filed Nov. 17, 2011, which claims priority from provisional application serial numbers U.S. 61/414,977 entitled, Development of Small Molecule Antibody Recruiting Therapeutics for the Treatment of HIV, ARM-HI13 Species and Synthetic Route, filed Nov. 18, 2010, and US61/522,518, filed Aug. 11, 2011, entitled, Bifunctional Molecules with Antibody-Recruiting and Entry Inhibitory Activity against the Human Immunodeficiency Virus, the entire contents of said applications being incorporated by reference herein.

This invention was made with government support under OD002913 awarded by National Institutes of Health. The government has certain rights in the invention.

FIELD OF THE INVENTION

The present invention relates to bifunctional molecules for inhibiting Human Immunodeficiency Virus (HIV) infection through binding to the HIV glycoprotein gp 120, while also engaging in antibody-recruiting for attracting and binding antibodies which combat the bound HIV.

BACKGROUND AND DISCUSSION OF THE INVENTION

In recent years, antibody based therapeutics have become important instruments in treating human disease. (Brekke, O. H.; Sandlie. I. Nat. Rev. Drug Discovery 2003, 2, 52-62.) Current antibody-based therapeutics function either by blocking the effector actions of pathological molecules, or by targeting specific epitopes on cell surfaces for immune-mediated destruction. However, these approaches suffer from certain limitations, including severe side effects, lack of oral bioavailability, and high cost. (Allen. T. M. Nat. Rev. Cancer 2002, 2, 750-763.) Thus, alternative methods are being sought that would still exploit the powerful cytolytic potential of antibodies already present in the human blood stream yet avoid many of these disadvantages.

Acquired Immune Deficiency Syndrome (AIDS) is a world-wide epidemic that has claimed many lives and severely debilitated many more through immune suppression. A great deal of effort has been directed toward the development of a vaccine for this disease, without success. The failure to develop an effective vaccine underscores the need for new prevention and treatment strategies toward this disease.

The human immune system is highly versatile in its ability to target and destroy foreign pathogens. HIV, however, is an elusive virus to the body's immune system which has evolved mechanisms both to evade and to destroy the immune response of human hosts in the process of causing AIDS. Researchers recently found that one of the shortfalls of the human immune system in combating HIV is also one the antibody's stronger point against other viruses; its structure.

An antibody is a Y-shaped molecule with two epitopes comprising antigen recognizing proteins on the two Y tips. These two epitopes allow the antibody to bind to two proteins on the antigen's surface, creating a stronger bond when compared to a one-epitope protein bond. Viruses have proteins extending from their viral coat, which are the proteins the antibodies bind to.

HIV has fewer proteins than normal viruses. The proteins are placed farther apart and this structural difference is believed responsible for the antibody's epitopes being unable to bind to two different HIV surface proteins (See Klein et al. "Examination of the contributions of size and avidity to the neutralization mechanisms of the anti-HIV antibodies b12 and 4E10" Proceedings of the National Academy of Sciences, 2009 Abstract).

HIV has also been shown to bind to a surface molecule known as the CD4 or T4 receptor, which is present on various cells susceptible to HIV infection, including T lymphocytes and macrophages. (See Shaw et al., Science 226, pp. 1165-1171 for a discussion of tropism of HTLV-III.)

A few methods for recruiting naturally occurring antibodies to cancer cells have appeared in the literature, but none are believed to have been explored directed to HIV (See Carlson, C.; Mowery, P.; Owen, R.; Dykhuizen, E. C.: Kiessling, L. ACS Chem. Biol. 2007, 2, 119-127; Owen. R.; Carlson, C; Xu, J.; Mowery, P.; Fasella, E.; Kiessling, L. ChemBioChem 2007, 8, 68-82; Popkov. M.: Gonzalez, E.; Sinha, S.; Barbas, C. Proc. Natl. Acad. Sci. U.S.A. 2009, 106, 4378-4383; Popkov, M.; Rader. C; Gonzalez, B.; Sinha. S.; Barbas, C. Intl. J. Cancer 2006, 119, 1194-1207; (25) Low, P.; Henne, W.; Doomeweerd, D. Acc. Chem. Res. 2008, 41, 120-129; Lu, Y.: You, F.; Vlahov, I.; Westrick. E.; Fan, M.; Low, P. S.; Leamon, C. P. Mol. Pharm. 2007, 4, 695-706.

(27) Rader. C.; Sinha, S. C.; Popkov, M.; Lerner, R. A.; Barbas, C. F. Proc. Natl. Acad. Sci. U.S.A. 2003, 100, 5396-5400), bacteria (Bertozzi, C. R.; Bednarski, M. D. J. Am. Chem. Soc. 1992, 114, 5543-5546; Bertozzi, C. R.; Bednarski. M. D. J. Am. Chem. Soc. 1992. 114, 2242-2245; Li, J.: Zacharek, S.; Chen, X.; Wang, J. Q.: Zhang, W.; Janczuk, A.; Wang, P. G. Bioorg. Med. Chem. 1999, 7, 1549-1558; Krishnamurthy, V. M.; Quinton, L. J.; Estroff L. A.; Metallo, S. J.; Isaacs, J. M.; Mizgerd, J. P; Whitesides, G. M. Biomaterials 2006, 27, 3663-3674), and viruses ((32) Shokat, K. M.; Schultz, P. G. J. Am. Chem. Soc. 1991, 113, 1861-1862; Naicker, K. P.: Li, H.; Heredia, A.; Song, H.; Wang, L. Org. Biomol. Chem. 2004, 2, 660-664; Perdomo, M. F.: Levi. M.; Ilberg, M. S.; Vahlne, A. Proc. Natl. Acad. Sci. U.S.A. 2008, 105, 6).

In the HIV realm, most approaches have relied upon protein- or peptide-based antibody targeting constructs. For example, Shokat and Schultz (Shokat, K. M.; Schultz, P. G. J. Am. Chem. Soc. 1991, 113, 1861-1862) first demonstrated that anti-DNP antibodies could be redirected to immobilized protein targets (gp120 and streptavidin) as a therapeutic strategy toward HIV. More recent work in this vein has employed peptide-R-Gal conjugates to target human anti-Gal antibodies to HIV-infected cells. (Naicker, K. P.: Li, H.;

Heredia, A.; Song, H.; Wang, L. Org. Biomol. Chem. 2004, 2, 660-664; Perdomo, M. F.: Levi. M.; Ilberg, M. S.; Vahlne, A. Proc. Natl. Acad. Sci. U.S.A. 2008, 105, 6)

While these peptide conjugates were shown to be effective in killing Env-expressing cells, they were also found to exhibit some non specific cytotoxicity. Bertozzi, C. R.; Bednarski, M. D. J. Am. Chem. Soc. 1992, 114, 5543-5546.

The present work sought to address these deficiencies, by providing compositions for treating HIV infection which can improve the immune system's ability to respond to HIV infection. We have discovered one way to assist the body is to recruit existing antibodies to attack HIV. Specifically, we have developed bifunctional molecules (Corson. T. W.; Aberle, N.; Crews, C. M. ACS Chem. Biol. 2008, 3, 677-692) capable of which inhibit the pathogenic behavior of HIV through two distinct mechanisms: (1) by interfering with viral entry via antagonism of the interaction between the viral envelope protein gp120 and the human protein CD4, and (2) by recruiting anti-dinitrophenyl ("anti-DNP") antibodies, a population of antibodies present in high concentrations in the human bloodstream, to the surface of the HIV virus and/or HIV-infected cells.

Antibodies recognizing the DNP epitope have been estimated to constitute 1% of circulating IgM and 0.8% of circulating IgG. See: (a) Karjalainen, K., Makela. O. Eur. J. Immunol. 1976, 6, 88-93. (b) Farah, F. S. Immunology 1973, 25, 217-226. The prevalence of anti-DNP antibodies has been estimated at between 18 and 90% of humans. See: (c) Ortega, E.; Kostovetzky. M.; Larralde, C. Mol. Immunol. 1984, 21, 883-888. (d) Jormalainen, S.; Makela. O. Eur. J. Immunol. 1971, 1, 471-478. Consequently, administration of a bifunctional molecule which can recruit these existing antibodies to attack HIV in a patient suffering from HIV infection may provide a basis for an effective treatment for the symptoms associated with HIV infection.

SUMMARY OF THE INVENTION

The present invention relates to ARM-HII ("Antibody-Recruiting Molecules targeting HIV Improved") compounds according to the general formula:

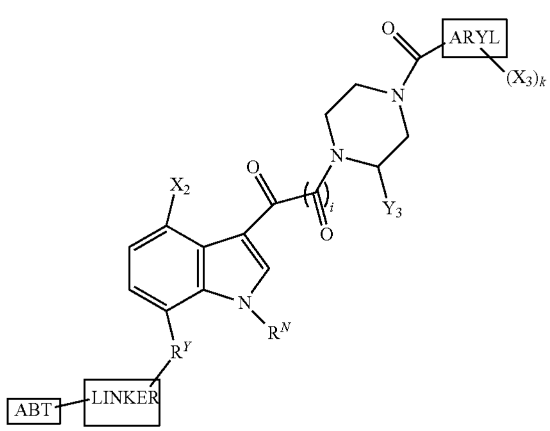

Where

ABT is an antibody binding terminus (moiety) comprising a hapten which is capable of binding to an antibody present in a patient (preferably a DNP group);

LINKER is a linker molecule which chemical links ABT to $R^Y$ or directly to the indole moiety at the carbon atom to which $R^Y$ is attached and which optionally includes a connector CT which may be a bond or a connector molecule;

ARYL is a an aromatic or heteroaromatic group, preferably a monocyclic or bicyclic aromatic or heteroaromatic group;

$R^Y$ is absent or is an optionally substituted aryl or heteroaryl group or O, $(CH_2)_j$, $NR^1$, —S—, —NHC(O)—, —NHC(O)NH—, S(O), $S(O)_2$, $—S(O)_2O$, $—OS(O)_2$, or $OS(O)_2O$ (the aryl or heteroaryl group also may be substituted with these and/or other groups and/or each of these groups also may link the aryl or heteroaryl group to the indole moiety);

$X_2$ is H, $—(CH_2)_nOH$, $—(CH_2)_nCOOH$, $C_1$-$C_6$ alkyl, $—(CH_2)_nO—(C_1\text{-}C_6$ alkyl), $—(CH_2)_nC(O)—(C_1\text{-}C_6$ alkyl), $—(CH_2)_nNHC(O)—R_1$, $—(CH_2)_nC(O)—NR_1R_2$, $—(CH_2O)_nH$, $—(CH_2O)_nCOOH$, $—(OCH_2)_nO—(C_1\text{-}C_6$ alkyl), $—(CH_2O)_nC(O)—(C_1\text{-}C_6$ alkyl), $—(OCH_2)_nNHC(O)—R_1$, $—(CH_2O)_nC(O)—NR_1R_2$, $NO_2$, CN or halogen (F, Cl, Br, I, preferably F or Cl);

$X_3$ is H, $—(CH_2)_nOH$, $—(CH_2)_nCOOH$, $C_1$-$C_6$ alkyl, $—(CH_2)_nO—(C_1\text{-}C_6$ alkyl), $—(CH_2)_nC(O)—(C_1\text{-}C_6$ alkyl), $—(CH_2)_nNHC(O)—R_1$, $—(CH_2)_nC(O)—NR_1R_2$, $—(CH_2O)_nH$, $—(CH_2O)_nCOOH$, $—(OCH_2)_nO—(C_1\text{-}C_6$ alkyl), $—(CH_2O)_nC(O)—(C_1\text{-}C_6$ alkyl), $—(OCH_2)_nNHC(O)—R_1$, $—(CH_2O)_nC(O)—NR_1R_2$, $NO_2$, CN, halogen (F, Cl, Br, I, preferably F or Cl) or a monocyclic aryl or heteroaryl group which itself is optionally substituted;

$R^1$ is H or a $C_1$-$C_3$ alkyl group;

$R_1$ and $R_2$ are each independently H or a $C_1$-$C_6$ alkyl group;

i is 0 or 1, preferably 1;

j is 1, 2 or 3;

k is 0, 1, 2 or 3, preferably 0, 1 or 2;

n is 0, 1, 2, 3, 4, 5, 6, preferably 0-3;

$Y_3$ is H or a $C_1$-$C_3$ alkyl group (preferably, disposed out of or into the plane, preferably out of the plane on the chiral carbon; and $R^N$ is H or a $C_1$-$C_3$ alkyl group which is optionally substituted with one or two hydroxyl groups or up to three halogen groups (preferably F)

or a pharmaceutically acceptable salt, enantiomer, solvate or polymorph thereof.

In other preferred aspects of the invention, compounds according to the present invention may be represented by the chemical structure:

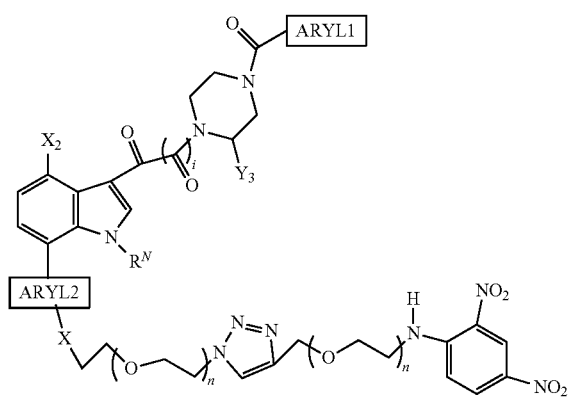

Where

ARYL1 is a monocyclic or bicyclic aryl or heteroaryl group according to the chemical structure:

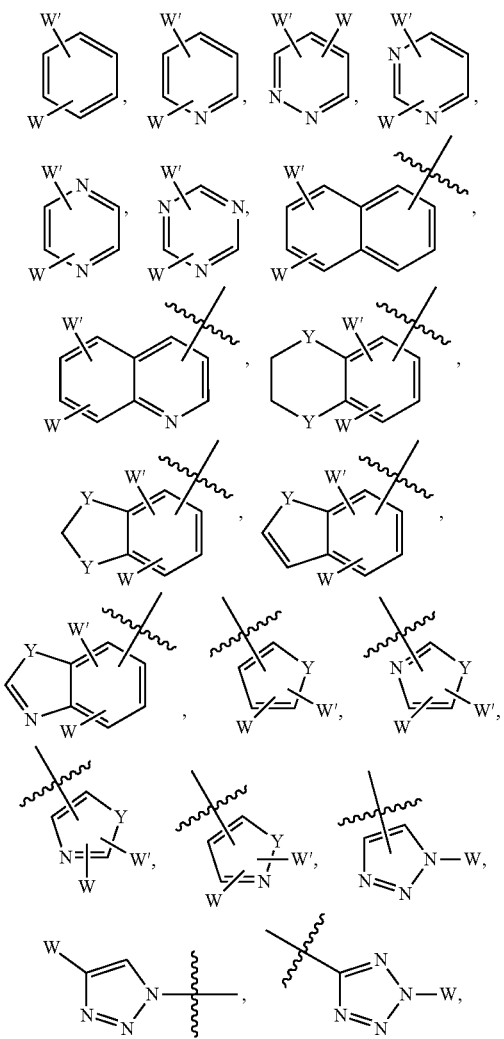

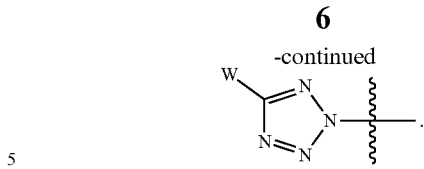

Where W is H, $-(CH_2)_nOH$, $-(CH_2)_nCOOH$, $C_1$-$C_6$ alkyl, $-(CH_2)_nO-(C_1$-$C_6$ alkyl), $-(CH_2)_nC(O)-(C_1$-$C_6$ alkyl), $-(CH_2)_nNHC(O)-R_1$, $-(CH_2)_nC(O)-NR_1R_2$, $-(CH_2O)_nH$, $-(CH_2O)_nCOOH$, $C_1$-$C_6$ alkyl, $-(CH_2O)_nO-(C_1$-$C_6$ alkyl), $-(CH_2O)_nC(O)-(C_1$-$C_6$ alkyl), $-(CH_2O)_nNHC(O)-R_1$, $-(CH_2O)_nC(O)-NR_1R_2$, $NO_2$, CN, halogen (F, Cl, Br, I, preferably F or Cl) or a monocyclic aryl or heteroaryl group which itself is optionally substituted (especially an optionally substituted benzoyl or benzyl group);

W' is H, $-(CH_2)_nOH$, $-(CH_2)_nCOOH$, $C_1$-$C_6$ alkyl, $-(CH_2)_nO-(C_1$-$C_6$ alkyl) or halogen (preferably F or Cl);

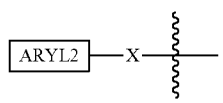

is a group according to chemical structure:

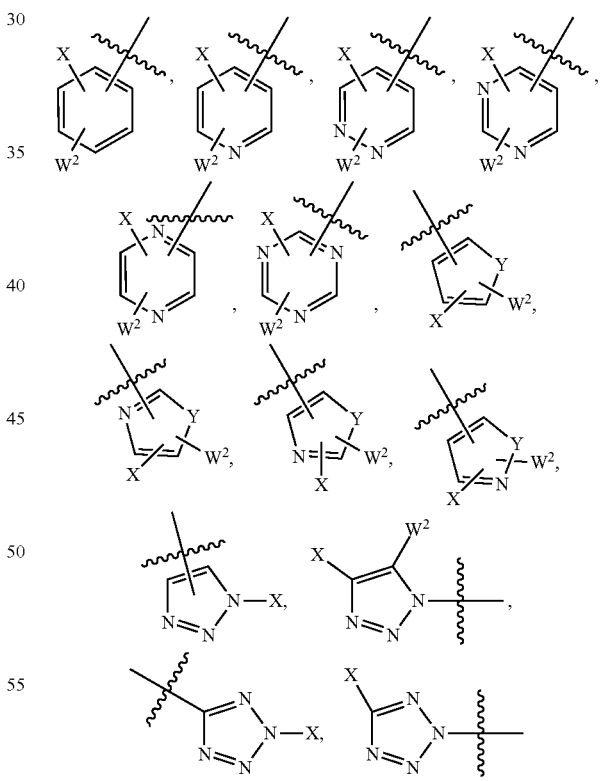

Where $W^2$ is H, $-(CH_2)_nOH$, $-(CH_2)_nCOOH$, $C_1$-$C_6$ alkyl, $-(CH_2)_nO-(C_1$-$C_6$ alkyl), $-(CH_2)_nC(O)-(C_1$-$C_6$ alkyl), $-(CH_2)_nNHC(O)-R_1$, $-(CH_2)_nC(O)-NR_1R_2$, $-(CH_2O)_nH$, $-(CH_2O)_nCOOH$, $C_1$-$C_6$ alkyl, $-(CH_2O)_nO-(C_1$-$C_6$ alkyl), $-(CH_2O)_nC(O)-(C_1$-$C_6$ alkyl), $-(CH_2O)_nNHC(O)-R_1$, $-(CH_2O)_nC(O)-NR_1R_2$, $NO_2$, CN or halogen (preferably F or Cl);

X is a a bond or a group —(CH$_2$)$_n$NH—, —(CH$_2$)$_n$NHC(O)—, —(CH$_2$)$_n$O—, —(CH$_2$)$_m$—, —(CH$_2$)$_n$S—, —(CH$_2$)$_n$S(O)—, —(CH$_2$)$_n$ SO$_2$— or —(CH$_2$)$_n$NH—C(O)—NH— which links

ARYL2 to the linker;

Y is O, S or N—R where R is H or a C$_1$-C$_3$ alkyl group;

X$_2$ is H, —(CH$_2$)$_n$OH, —(CH$_2$)$_n$COOH, C$_1$-C$_6$ alkyl, —(CH$_2$)$_n$O—(C$_1$-C$_6$ alkyl), —(CH$_2$)$_n$C(O)—(C$_1$-C$_6$ alkyl), —(CH$_2$)$_n$NHC(O)—R$_1$, —(CH$_2$)$_n$C(O)—NR$_1$R$_2$, —(CH$_2$O)$_n$H, —(CH$_2$O)$_n$COOH, C$_1$-C$_6$ alkyl, —(OCH$_2$)$_n$O—(C$_1$-C$_6$ alkyl), —(CH$_2$O)$_n$C(O)—(C$_1$-C$_6$ alkyl), —(OCH$_2$)$_n$NHC(O)—R$_1$ or —(CH$_2$O)$_n$C(O)—NR$_1$R$_2$;

R$_1$ and R$_2$ are each independently H or a C$_1$-C$_6$ alkyl group;

Y$_3$ is H or a C$_1$-C$_3$ alkyl group (preferably, disposed out of or into the plane, preferably out of the plane on the chiral carbon; and R$^N$ is H or a C$_1$-C$_3$ alkyl group which is optionally substituted with one or two hydroxyl groups or up to three halogen groups (preferably F);

i is 0 or 1, preferably 1;

m is 1, 2, 3, 4 or 5, preferably 1, 2 or 3, more preferably 1; and

Each n is independently 0, 1, 2, 3, 4, 5 or 6, preferably 0, 1, 2 or 3, or a pharmaceutically acceptable salt, enantiomer, solvate or polymorph thereof.

Preferred bifunctional compounds for use in the present invention include those where R$^Y$ is an optionally substituted aryl or heteroaryl group as otherwise described herein, preferably an optionally substituted phenyl (especially a C$_1$-C$_6$ alkyl, hydroxyl, methylalcohol), naphthyl, pyridyl (2-, 3- or 4-pyridyl group), thiazolyl (2-, 4- or 5-thiazole), isothiazolyl, oxazolyl (2-, 4- or 5-oxazole), isoxazolyl, furanyl (2- or 3-furan) or thiophenyl (2- or 3-thiophene). The R$^Y$ group is preferably substituted with a —NH—, —NHCO—, —O—, —CH$_2$—, —S— or —NHC(O)NH— group which links the R$^Y$ group (preferably as an aryl or heteroaryl group) to the linker group. R$^N$ is preferably H, X$_2$ is preferably H or OCH$_3$; X$_3$ is preferably H, OCH$_3$ or CH$_3$; Y$_3$ is H or CH$_3$ (racemic or enantiomeric); i is preferably 1, or a pharmaceutically acceptable salt, enantiomer, solvate or polymorph thereof. Preferred Aryl1 groups include the groups which appear in the Table 1, hereinbelow and include phenyl, o-, m-, or p-toluyl, o-, m- or p-ethylphenyl, o-, m- or p-isopropylphenyl, naphthyl (preferably 1- or 2-), o-, m- or p-phenol, 3,5-dihydroxylphenyl, o-, m- or p-hydroxymethylphenyl or a 2-, 3-, or 4-pyridyl group.

Preferred

groups for use in compounds according to the present invention may be represented by the chemical structure (which includes a connector triazole molecule:

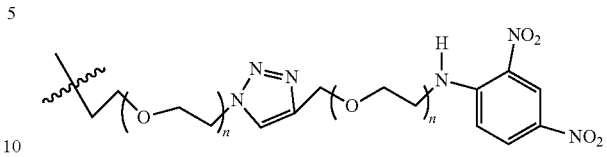

Where each n is independently 0, 1, 2, 3, 4, 5 or 6, preferably 0, 1, 2 or 3. Other linker and ABT groups which may be used are described in the specification above and in the examples.

In an additional aspect of the invention, a pharmaceutical composition comprises an effective amount of a bifunctional compound as described above, optionally and preferably in combination with a pharmaceutically acceptable carrier, additive or excipient. In alternative aspects, pharmaceutical combination compositions comprise an effective amount of a bifunctional compound as described herein, in combination with at least one additional agent which is used to treat HIV.

In a further aspect of the invention, compounds according to the present invention are used to treat and/or reduce the likelihood of an HIV infection or a secondary effect of HIV (such as AIDS, ARC and related disease states or conditions which occur secondary to an HIV infection) in a patient. The method of treating and/or reducing the likelihood of an HIV infection or secondary effect of an HIV cancer comprises administering to a patient in need an effective amount of a bifunctional compound as otherwise described herein in combination with a pharmaceutically acceptable carrier, additive or excipient, optionally in further combination with at least one additional agent which is effective in treating and/or reducing the likelihood of an HIV infection, or one or more of its secondary conditions or effects.

The present invention also relates to instances in which destruction of CD4 cells which are infected with HIV (HIV+CD4 cells) may be useful to inhibit latent HIV infections from becoming active. In this aspect of the invention, destruction of HIV+CD4 cells in an HIV positive patient may be used to inhibit or more completely eradicate an HIV infection and/or reduce the likelihood of an occurrence or recurrence of HIV in a patient who is HIV positive.

The present invention also relates to a method for binding and eliminating HIV in a patient comprising administering to a patient infected with HIV, an effective amount of a bifunctional compound as otherwise described herein.

Thus, the present invention presents unique, non-peptidic, bifunctional molecules which can operate through the bifunctional mechanisms specified above in treating HIV.

The realization that viruses may exert cell and tissue tropism by attachment at highly specific sites on cell membrane receptors has encouraged investigators in the past to seek agents which would bind at the viral receptor sites of cell membranes and thus prevent binding of a specific virus to these cells.

Specifically, HIV has been shown to bind to a surface molecule known as the CD4 or T4 receptor which is present on various cells susceptible to HIV infection, including T lymphocytes and macrophages. The binding occurs via the HIV envelope protein, gp120.

It is an object of the present invention to provide bifunctional compounds that would act to alleviate the symptoms of AIDS by binding a bifunctional molecule which has a first terminus for binding to the gp120 envelope protein, the bifunctional molecule having a second antibody recruiting terminus which attracts antibodies already circulating throughout the body, to form a ternary complex between anti-DNP antibodies and gp120 and/or gp120-expressing cells, the antibodies attacking the HIV engaged by the bifunctional molecule. These bifunctional (which term also includes multifunctional) molecules are thus generically referred to herein as "Antibody-Recruiting Molecules targeting HIV Improved" or "ARM-HII".

The inventive ARM-HII molecules are "bifunctional" in that they possess a at least one pathogen binding terminus (PBT) and at least one antibody recruiting terminus (ABT) connected by at least one linker and a connector molecule. The PBT is designed to bind to the HIV glycoprotein gp120 (gp120 on the viral membrane as well as gp120 displayed on infected cells). The ABT is designed to bind and/or recruit antibodies to the site of the binding of the bifunctional compound according to the present invention.

In one embodiment of the invention, a bifunctional ARM-HI molecule is described which is capable of redirecting a population of anti-hapten (e.g. anti-dinitrophenyl or anti-DNP) antibodies, which represent a population of antibodies present in high concentrations in the human blood stream ("endogenous antibodies"), to the HIV gp120 Env gene product. The Env glycoprotein, a complex between gp120 and membrane-bound gp 41, is expressed on both the surface of the HIV virus and on virus-infected cells, especially CD4 cells. (Miranda. L. R.; Schaefer, B. C.; Kupfer. A.; Hu, Z. X.; Franzusoff, A. Proc. Natl. Acad. Sci. U.S.A, 2002, 99, 8031-8036). The gp120 component of Env mediates the first step in viral entry into human cells by binding the protein CD4.

According to the present invention, a ternary complex is formed between anti-hapten (e.g. DNP or other hapten) antibodies, ARM-HII, and Env-expressing cells which mediates the complement-dependent destruction of these cells. Further, since ARM-HI binds gp120 competitively with CD4, it also inhibits the entry of live HIV into human T-cells. Thus, ARM-HI has the potential to interfere with the survival of HIV through multiple complementary mechanisms, and may also function as a prophylactic.

The ARM-HII compounds of the invention are unique in that they represent a molecule-based, not a peptide and/or protein based, anti-HIV strategy for targeting the virus life cycle through mutually reinforcing molecular mechanisms, inhibiting virus entry while targeting Env-expressing cells for immune recognition and clearance. In general, the ARM-HII molecules have certain advantages over proteins from a therapeutic standpoint because of their low propensity for immunogenicity, high metabolic stability, ready large-scale production, and relatively low cost. Molecule based antibody-recruiting therapeutics such as ARM-HII have additional benefits over available treatment approaches to HIV. For example, directing HIV-infected cells and virus particles to Fcγ receptors on antigen-presenting cells enhances the presentation of viral antigens on MHC proteins and contributes to long-lasting anti-HIV immunity. (See Lu, Y.: You, F.; Vlahov, I.; Westrick. E.; Fan, M.; Low, P. S.; Leamon, C. P. Mol. Pharm. 2007, 4, 695-706, Rawool, D. B.; Bitsaktsis, C.; Li, Y.; Gosselin, D. R., Lin, Y.; Kurkure, N. Y.; Metzger, D. W.; Gosselin, E. J. J. Immunol, 2008, 180, 5548-5557) Critically, no non specific cytotoxicity was observed in either MT-2 or CHO cell lines in response to the inventive ARM-HI molecules, limiting the possibility of encountering serious side effects from treatment therewith.

Furthermore, because anti-hapten (anti-DNP) antibodies are already present in the human blood stream, no pre-vaccination is necessary for ARM-HI activity. Also, the binding of bifunctional molecule targeting agents to antibodies should prolong their plasma half-life, thus increasing their effectiveness. (See Rader. C.; Sinha, S. C.; Popkov, M.; Lerner, R. A.; Barbas, C. F. Proc. Natl. Acad. Sci. U.S.A. 2003, 100, 5396-5400)

Elucidation of the molecular details governing the interactions among ARM-HI, gp120, and anti-DNP antibodies assists in optimization efforts as well as in the evaluation of this strategy in more complex biological models of HIV infection.

As stated above, the invention is directed to "bifunctional" molecules, the inventive molecules being "bifunctional" in that they possess a pathogen binding terminus (PBT) and an antibody recruiting terminus (ABT) connected by a linker. The PBT is designed to bind to the HIV glycoprotein gp120 (gp120 on the viral membrane as well as gp120 displayed on infected cells). The ABT is designed to bind antibodies and therefore redirect endogenous antibodies and hence the immune response to the pathogen. Formation of a ternary complex between these molecules, the antibodies, and the target pathogen, leads to targeted cytotoxicity through various mechanisms including antibody dependent cellular cytotoxicity (ADCC), or complement-dependent cytotoxicity (CDC).

The present invention is directed to pharmaceutical compositions comprising the above-described bifunctional molecules that can inhibit HIV entry into a target cell, while also recruiting antibodies to attack the HIV or an HIV infected cell, in a pharmaceutically acceptable carrier. As an aspect of the invention, therefore, we provide a pharmaceutical composition comprising a bifunctional molecule compound of the invention in association with a pharmaceutically acceptable carrier or excipient, adapted for use in human or veterinary medicine. Such compositions may be presented for use in conventional manner in admixture with one or more physiologically acceptable carriers or excipients. The compositions may optionally further contain one or more other therapeutic agents which may, if desired, be a different antiviral agent.

The bifunctional molecule compounds according to the invention may be formulated for oral, buccal, nasal, parenteral, topical or rectal administration, among others, as otherwise described herein.

In particular, the bifunctional compounds according to the invention may be formulated for injection or for infusion and may be presented in unit dose form in ampoules or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle, e.g. sterile, pyrogen-free water, before use.

The pharmaceutical compositions according to the invention may also contain other active ingredients such as antimicrobial agents, or preservatives.

The compositions may contain from 0.001-99% of the active material.

The invention further provides a process for preparing a pharmaceutical composition which comprises bringing a bifunctional molecule compound of the invention into association with a pharmaceutically acceptable excipient or carrier.

For administration by injection or infusion, dosages and desired drug concentrations of the disclosed pharmaceutical compositions may vary depending on the particular use, patient condition, age, drug tolerance, etc., as would be understood by one skilled in the field. Consequently, the determination of an appropriate dosage and/or route of administration is well within the skill of an ordinary practitioner, and the compounds can certainly be formulated without undue experimentation for administration in the treatment of humans, for example, using standard and well known dose-response protocols.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other ARM-HI compound which may be used to treat HIV infection or a secondary effect or condition thereof.

DETAILED DESCRIPTION OF THE INVENTION

Figure 1:
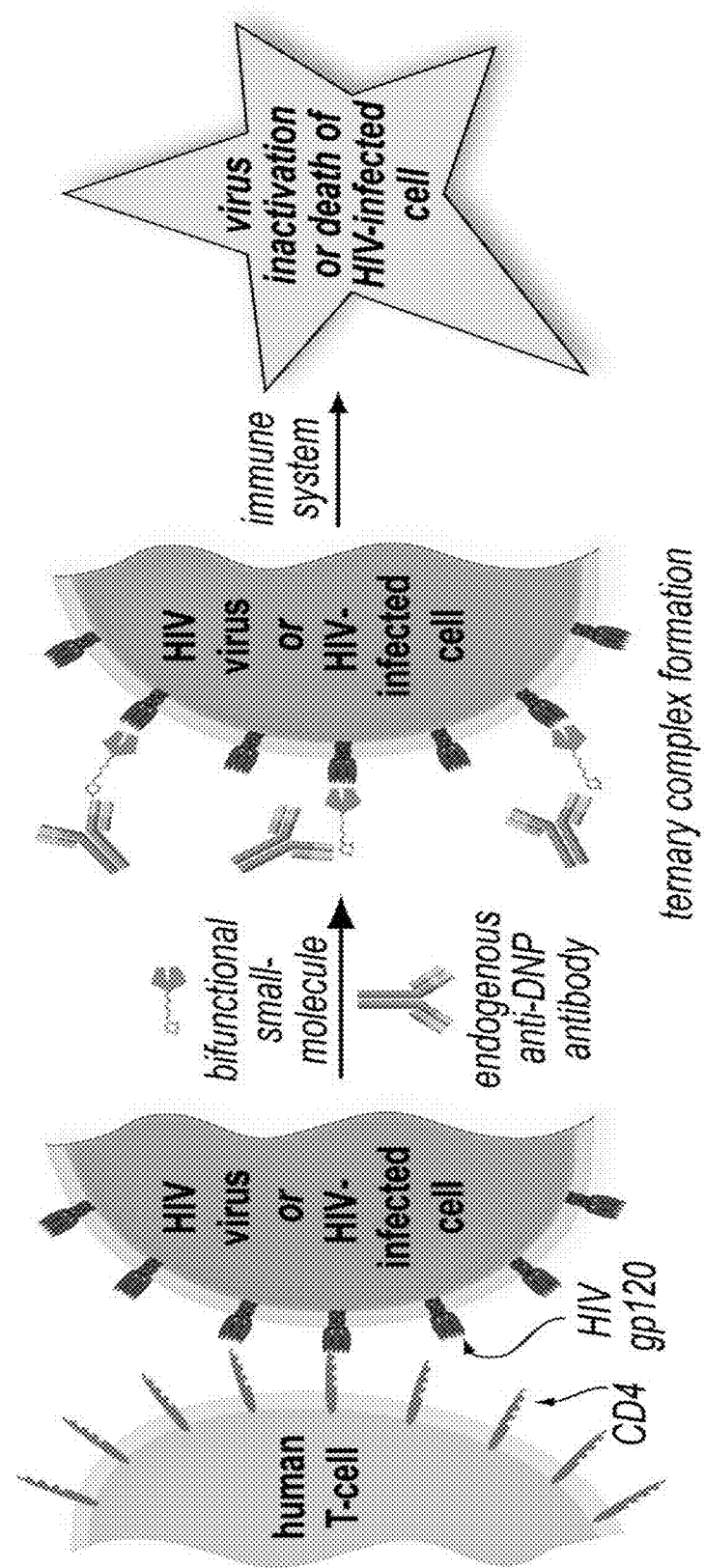
FIG. 1 illustrates the effects of bifunctional ARM-HI compounds in forming a ternary complex between gp120 and an antibody.
Figure 2:
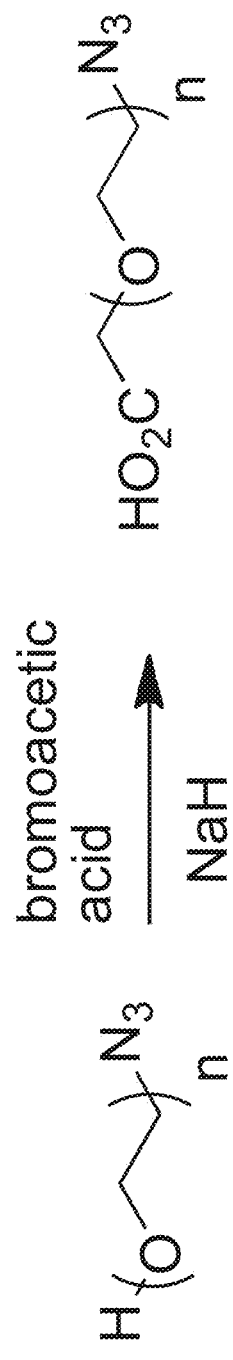
FIG. 2 illustrates the dual mechanism of action exhibited by the bifunctional molecules of the present invention.

The following terms are used to describe the present invention. In instances where a term is not specifically defined herein, that term is given an art-recognized meaning by those of ordinary skill applying that term in context to its use in describing the present invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The term "compound", as used herein, unless otherwise indicated, refers to any specific chemical compound disclosed herein and includes tautomers, regioisomers, geometric isomers, and where applicable, optical isomers (enantiomers) thereof, as well as pharmaceutically acceptable salts and derivatives (including prodrug forms) thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents, linkers and connector molecules and variables associated with same, among others, are described. It is understood by those of ordinary skill that molecules which are described herein are stable compounds as generally described hereunder.

"Alkyl" refers to a fully saturated monovalent radical containing carbon and hydrogen, and which may be cyclic, branched or a straight chain. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl, among others. Preferred alkyl groups are $C_1$-$C_6$ or $C_1$-$C_3$ alkyl groups.

"Aryl" or "aromatic", in context, refers to a substituted (as otherwise described herein) or unsubstituted monovalent aromatic radical having a single ring (e.g., benzene or phenyl) or condensed rings (e.g., naphthyl, anthracenyl, phenanthrenyl, etc.) and can be bound to the compound according to the present invention at any available stable position on the ring(s) or as otherwise indicated in the chemical structure presented. Other examples of aryl groups, in context, may include heterocyclic aromatic ring systems "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others.

Alternative aryl and heteroaryl groups according to the present invention preferably include, for example, phenyl, naphthyl, pyridyl (2-, 3- or 4-pyridyl group), thiazolyl (2-, 4- or 5-thiazole), isothiazolyl, oxazolyl (2-, 4- or 5-oxazole), isoxazolyl, furanyl (2- or 3-furan) or thiophenyl (2- or 3-thiophene). Monocyclic and bicyclic aryl and heteroayl groups are as otherwise described herein.

In alternative embodiments, preferred heteroaryl groups are 5- or 6-membered aryl or heteroaryl group according to the chemical structure:

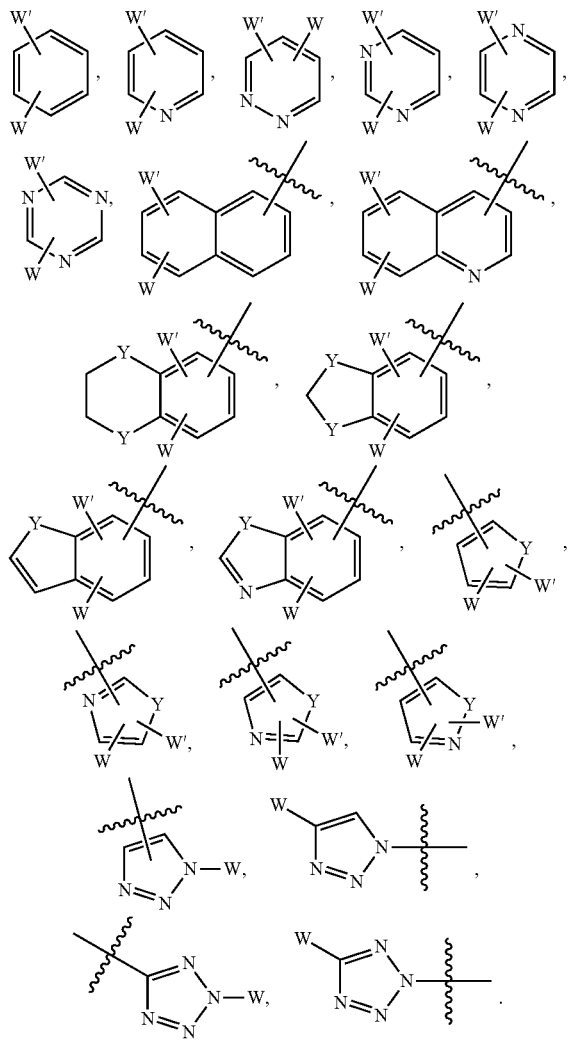

Where W is H, —(CH$_2$)$_n$OH, —(CH$_2$)$_n$COOH, C$_1$-C$_6$ alkyl, —(CH$_2$)$_n$O—(C$_1$-C$_6$ alkyl), —(CH$_2$)$_n$C(O)—(C$_1$-C$_6$ alkyl), —(CH$_2$)$_n$NHC(O)—R$_1$, —(CH$_2$)$_n$C(O)—NR$_1$R$_2$, —(CH$_2$O)$_n$OH, —(CH$_2$O)$_n$COOH, C$_1$-C$_6$ alkyl, —(CH$_2$O)$_n$O—(C$_1$-C$_6$ alkyl), —(CH$_2$O)$_n$C(O)—(C$_1$-C$_6$ alkyl), —(CH$_2$O)$_n$NHC(O)—R$_1$, —(CH$_2$O)$_n$C(O)—NR$_1$R$_2$, NO$_2$, CN, halogen (F, Cl, Br, I, preferably F or Cl) or a monocyclic aryl or heteroaryl group which itself is optionally substituted (especially an optionally substituted benzoyl or benzyl group);
W' is H, —(CH$_2$)$_n$OH, —(CH$_2$)$_n$COOH, C$_1$-C$_6$ alkyl, —(CH$_2$)$_n$O—(C$_1$-C$_6$ alkyl) or halogen (preferably F or Cl); and
Y is O, S or N—R, where R is H or a C$_1$-C$_3$ alkyl group.

In still other embodiments, preferred aryl or heteroaryl groups include those which are substituted according to the chemical structures:

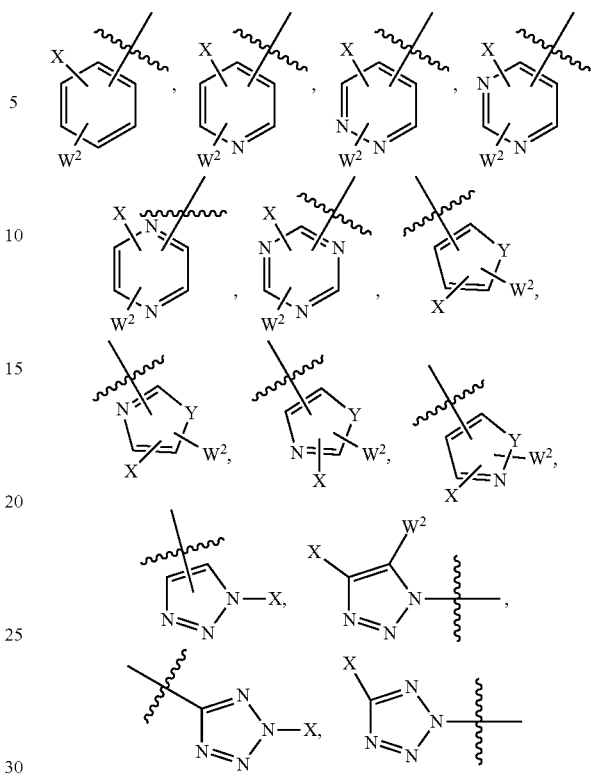

Where W$^2$ is H, —(CH$_2$)$_n$OH, —(CH$_2$)$_n$COOH, C$_1$-C$_6$ alkyl, —(CH$_2$)$_n$O—(C$_1$-C$_6$ alkyl), —(CH$_2$)$_n$C(O)—(C$_1$-C$_6$ alkyl), —(CH$_2$)$_n$NHC(O)—R$_1$, —(CH$_2$)$_n$C(O)—NR$_1$R$_2$, —(CH$_2$O)$_n$OH, —(CH$_2$O)$_n$COOH, C$_1$-C$_6$ alkyl, —(CH$_2$O)$_n$O—(C$_1$-C$_6$ alkyl), —(CH$_2$O)$_n$C(O)—(C$_1$-C$_6$ alkyl), —(CH$_2$O)$_n$NHC(O)—R$_1$, —(CH$_2$O)$_n$C(O)—NR$_1$R$_2$, NO$_2$, CN or halogen (preferably F or Cl);
X is a group —NH—, —NHC(O)—, —O—, —(CH$_2$)$_m$—, —S—, —S(O)—, SO$_2$— or —NH—C(O)—NH—; and
Y is O, S or N—R, where R is H or a C$_1$-C$_3$ alkyl group.

The term "substituted" shall mean substituted at a carbon (or nitrogen) position within context, hydroxyl, carboxyl, cyano (C≡N), nitro (NO$_2$), halogen (preferably, 1, 2 or 3 halogens, especially on an alkyl, especially a methyl group such as a trifluoromethyl), alkyl group (preferably, C$_1$-C$_{10}$, more preferably, C$_1$-C$_6$), aryl (especially phenyl and substituted phenyl for example benzyl or benzoyl), alkoxy group (preferably, C$_1$-C$_6$ alkyl or aryl, including phenyl and substituted phenyl), ester (preferably, C$_1$-C$_6$ alkyl or aryl) including alkylene ester (such that attachment is on the alkylene group, rather than at the ester function which is preferably substituted with a C$_1$-C$_6$ alkyl or aryl group), preferably, C$_1$-C$_6$ alkyl or aryl, halogen (preferably, F or Cl), nitro or amine (including a five- or six-membered cyclic alkylene amine, further including a C$_1$-C$_6$ alkyl amine or C$_1$-C$_6$ dialkyl amine which alkyl groups may be substituted with one or two hydroxyl groups), amido, which is preferably substituted with one or two C$_1$-C$_6$ alkyl groups (including a carboxamide which is substituted with one or two C$_1$-C$_6$ alkyl groups), alkanol (preferably, C$_1$-C$_6$ alkyl or aryl), or alkanoic acid (preferably, C$_1$-C$_6$ alkyl or aryl). The term "substituted" shall also mean within its context of use alkyl, alkoxy, halogen, amido, carboxamido, keto, carboxy, ester, keto, nitro, cyano and amine (especially including mono- or di-C$_1$-C$_6$ alkyl substituted amines which may be optionally substituted with one or two hydroxyl groups). In certain embodiments preferred substituents will include for example, —NH—, —NHC(O)—, —O—, —(CH$_2$)$_m$— (m and n are at least 1 as otherwise described herein), —S—, —S(O)—, SO$_2$— or —NH—C(O)—NH—, —(CH$_2$)$_n$OH, —(CH$_2$)$_n$COOH, C$_1$-C$_6$ alkyl, —(CH$_2$)$_n$O—(C$_1$-C$_6$ alkyl), —(CH$_2$)$_n$C(O)—(C$_1$-C$_6$ alkyl), —(CH$_2$)$_n$NHC(O)—R$_1$, —(CH$_2$)$_n$C(O)—NR$_1$R$_2$, —(CH$_2$O)$_n$OH, —(CH$_2$O)$_n$COOH, C$_1$-C$_6$ alkyl, —(OCH$_2$)$_n$O—(C$_1$-C$_6$ alkyl), —(OCH$_2$)$_n$C(O)—(C$_1$-C$_6$ alkyl), —(OCH$_2$)$_n$NHC(O)—R$_1$, —(CH$_2$O)$_n$C(O)—NR$_1$R$_2$, NO$_2$, CN or halogen (F, Cl, Br, I, preferably F or Cl), depending on the context of the use of the substituent.

Any substitutable position in a compound according to the present invention may be substituted in the present invention, but no more than 3, more preferably no more than 2 substituents (in some instances only 1 or no substituents) is present on a ring. Preferably, the term "unsubstituted" shall mean substituted with one or more H atoms.

The term "patient" or "subject" is used throughout the specification within context to describe an animal, generally a mammal and preferably a human, to whom treatment, including prophylactic treatment (prophylaxis), with the compositions according to the present invention is provided. For treatment of those infections, conditions or disease states which are specific for a specific animal such as a human patient or a patient of a particular gender, such as a human male patient, the term patient refers to that specific animal. Compounds according to the present invention are useful for treating and/or reducing the likelihood of HIV infections or the secondary effects of HIV infections, especially including AIDS and/or ARC.

The term "effective" is used herein, unless otherwise indicated, to describe an amount of a compound or composition which, in context, is used to produce or effect an intended result, whether that result relates to the inhibition of the effects of a toxicant on a subject or the treatment of a subject for secondary conditions, disease states or manifestations of exposure to toxicants as otherwise described herein. This term subsumes all other effective amount or effective concentration terms (including the term "therapeutically effective") which are otherwise described in the present application.

The terms "treat", "treating", and "treatment", etc., as used herein, refer to any action providing a benefit to a patient at risk for HIV infection or having an HIV infection, including improvement in the condition through lessening or suppression of titers of HIV or at least one symptom of HIV, prevention or delay in progression of the disease, prevention or delay in the onset of disease states or conditions which occur secondary to HIV, including AIDS or ARC, among others. Treatment, as used herein, encompasses both prophylactic and therapeutic treatment. The term "prophylactic" when used, means to reduce the likelihood of an occurrence or the severity of an occurrence within the context of the treatment of HIV, as otherwise described hereinabove.

The term "human immunodeficieincy virus" or "HIV" shall be used to describe human immunodeficiency viruses 1 and 2 (HIV-1 and HIV-2), the growth or replication of which may be inhibited or disease states of which may be treated using one or more methods according to the present invention. Viruses which may be treated according to the present invention include, for example, human immunodeficiency viruses 1 and 2 (HIV-1 and HIV-2), among others. The term HIV includes mutant strains of HIV including "drug resistant" or "multiple drug resistant" strains of the HIV virus which have mutated to be resistant to one or more clinically approved anti-HIV agents, including, in particular, HIV strains which are resistant to one or more NRTI compounds and/or NNRTI compounds. Exemplary HIV drug resistant strains which may be effectively treated using compounds according to the present invention include the following, among others: (defined by their reverse transcriptase or RT mutation)—XXBRU, K65R, Y115F, F116Y, Q151M, M184V, L74V, V75T, 4XZT, T215Y, K103N, T215Y/M184V, 5705-72, 488-101, C910-6, LA1M184V, G910-6 L100I, K101E, K103N, V106A, D110E, V179D, Y181C, D185E, D186E, Y188H, G190E, E138K, M41L, D67N, K70R, T215Y/F, K219Q/E, Y181C, K103N, L100I, Y188C/H, among others, including HIV-1 isolates JR-FL, ADA, HXBc2, SF162 and BaL, among others.

The terms "ARC" and "AIDS" refer to syndromes of the immune system caused by the human immunodeficiency virus, which are characterized by susceptibility to certain diseases and T cell counts which are depressed compared to normal counts. HIV progresses from Category 1 (Asymptomatic HIV Disease) to Category 2 (ARC), to Category 3 (AIDS), with the severity of the disease.

A Category 1 HIV infection is characterized by the patient or subject being HIV positive, asymptomatic (no symptoms) and having never had fewer than 500 CD4 cells. If the patient has had any of the AIDS-defining diseases listed for categories 2 (ARC) or 3 (AIDS), then the patient is not in this category. If the patient's t-cell count has ever dropped below 500, that patient is considered either Category 2 (ARC) or Category 3 (AIDS).

A Category 2 (ARC) infection is characterized by the following criteria: The patient's T-cells have dropped below 500 but never below 200, and that patient has never had any Category 3 diseases (as set forth below) but have had at least one of the following defining illnesses—

Bacillary angiomatosis
Candidiasis, oropharyngeal (thrush)
Candidiasis, vulvovaginal; persistent, frequent, or poorly responsive to therapy
Cervical dysplasia (moderate or severe)/cervical carcinoma in situ
Constitutional symptoms, such as fever (38.5 C) or diarrhea lasting longer than 1 month
Hairy leukoplakia, oral
Herpes zoster (shingles), involving at least two distinct episodes or more than one dermatome
Idiopathic thrombocytopenic purpura
Listeriosis
Pelvic inflammatory disease, particularly if complicated by tubo-ovarian abscess
Peripheral neuropathy
According to the U.S. government, in Category 2 ARC, the immune system shows some signs of damage but it isn't life-threatening.

A Category 3 (AIDS) infection is characterized by the following criteria: T-cells have dropped below 200 or the patient has had at least one of the following defining illnesses—

Brain Toxoplasmosis
Candidiasis of bronchi, trachea, or lungs
Candidiasis, esophageal
Cervical cancer, invasive**
Coccidioidomycosis, disseminated or extrapulmonary
Cryptococcosis, extrapulmonary
Cryptosporidiosis, chronic intestinal (greater than 1 month's duration)

Cytomegalovirus disease (other than liver, spleen, or nodes)
Cytomegalovirus retinitis (with loss of vision)
Encephalopathy, HIV-related
Herpes simplex: chronic ulcer(s) (greater than 1 month's duration); or bronchitis, pneumonitis, or esophagitis
Histoplasmosis, disseminated or extrapulmonary
Isosporiasis, chronic intestinal (greater than 1 month's duration)
Kaposi's sarcoma
Lymphoma, Burkitt's (or equivalent term)
Lymphoma, immunoblastic (or equivalent term)
Lymphoma, primary, of brain
*Mycobacterium avium* complex or *M. kansasii*, disseminated or extrapulmonary
*Mycobacterium tuberculosis*, any site (pulmonary** or extrapulmonary)
*Mycobacterium*, other species or unidentified species, disseminated or extrapulmonary
*Pneumocystis carinii* pneumonia
Pneumonia, recurrent
Progressive multifocal leukoencephalopathy
*Salmonella* septicemia, recurrent
Wasting syndrome due to HIV The term "coadministration" or "combination therapy" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided that effective concentrations of all coadministered compounds or compositions are found in the subject at a given time. In certain preferred aspects of the present invention, one or more of the bifunction ARM-HI compounds described above, are coadministered in combination with at least one additional anti-HIV agent as otherwise described herein in a cocktail for the treatment of HIV infections. In particularly preferred aspects of the invention, the coadministration of compounds results in synergistic anti-HIV activity of the therapy.

The term "additional anti-HIV agent" shall mean a traditional anti-HIV agent (ie., a non-bifunctional ARM-HI compound as otherwise described herein) which may be co-administered to a patient along with ARM-HI compounds according to the present invention in treating a patient for HIV. Such compounds include, for example, agents such as nucleoside reverse transcriptase inhibitors (NRTI), non-nucloeoside reverse transcriptase inhibitors, protease inhibitors and fusion inhibitors. Exemplary compounds include, for example, Amprenivir, Abacavir, Acemannan, Acyclovir, AD-439, AD-519, Adefovir dipivoxil, Alpha Interferon, Ansamycin, 097, AR 177, Beta-fluoro-ddA, BMS-232623 (CGP-73547), BMS-234475 (CGP-61755), CI-1012, Cidofovir, Curdlan sulfate, Cytomegalovirus Immune globin, Ganciclovir, Dideoxyinosine, DMP-450, Efavirenz (DMP-266), EL10, Famciclovir, FTC, GS 840, HBY097, Hypericin, Recombinant Human Interferon Beta, Interferon alfa-n3, Indinavir, ISIS-2922, KNI-272, Lamivudine (3TC), Lobucavir, Nelfinavir, Nevirapine, Novapren, Peptide T Octapeptide Sequence, Trisodium Phosphonoformate, PNU-140690, Probucol, RBC-CD4, Ritonavir, Saquinavir, Valaciclovir, Virazole Ribavirin, VX-478, Zalcitabine, Zidovudine (AZT), Tenofovir diisoproxil fumarate salt, Combivir, Abacavir succinate, T-20), AS-101, Bropirimine, CL246, EL10, FP-21399, Gamma Interferon, Granulocyte Macrophage Colony Stimulating Factor (GM-CSF), HIV Core Particle Immunostimulant, Interleukin-2 (IL-2), Immune Globulin Intravenous, IMREG-1, IMREG-2, Imuthiol Diethyl Dithio Carbamate, Alpha-2 Interferon, Methionine-Enkephalin, MTP-PE (Muramyl-Tripeptide), Granulocyte Colony Stimulating Factor (GCSF), Remune, rCD4 (Recombinant Soluble Human CD4-IgG), rCD4-IgG Hybrids, Recombinant Soluble Human CD4, Interferon Alfa 2a, SK&F1-6528, Soluble T4, Thymopentin, Tumor Necrosis Factor (TNF), AK602, Alovudine, Amdoxovir, AMD070, Atazanavir (Reyataz), AVX754 (apricitabine), Bevirimat, BI-201, BMS-378806, BMS-488043, BMS-707035, C31G, Carbopol 974P, Calanolide A, Carrageenan, Cellulose sulfate, Cyanovirin-N, Darunavir, Delavirdine, Didanosine (Videx), Efavirenz, Elvucitabine, Emtricitabine, Fosamprenavir (Lexiva), Fozivudine tidoxil, GS 9137, GSK-873,140 (aplaviroc), GSK-364735, GW640385 (brecanavir), HG0004, HGTV43, INCB9471, KP-1461, Lopinavir, Mifepristone (VGX410), MK-0518, PPL-100, PRO 140, PRO 542, PRO 2000, Racivir, SCH-D (vicriviroc), SPO1A, SPL7013, TAK-652, Tipranavir (Aptivus), TNX-355, TMC125 (etravirine), UC-781, UK-427,857 (Maraviroc), Valproic acid, VRX496, Zalcitabine, Valganciclovir, Clindamycin with Primaquine, Fluconazole Pastille, Nystatin Pastille, Eflornithine, Pentamidine, Isethionate, Trimethoprim, Trimethoprim/sulfa, Piritrexim, Pentamidine isethionate, Spiramycin, Intraconazole-R51211, Trimetrexate, Daunorubicin, Recombinant Human Erythropoietin, Recombinant Human Growth Hormone, Megestrol Acetate, Testosterone, Aldesleukin (Proleukin), Amphotericin B, Azithromycin (Zithromax), Calcium hydroxyapatite, Doxorubicin, Dronabinol, Entecavir, Epoetin alfa, Etoposide, Fluconazole, Isoniazid, Itraconazole (Sporanox), Megestrol, Paclitaxel (Taxol), Peginterferon alfa-2, Poly-L-lactic acid (Sculptra), Rifabutin (Mycobutin), Rifampin, Somatropin and Sulfamethoxazole/ Trimethoprim. Preferred anti-HIV compounds for use in the present invention include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof.

The term "pharmaceutically acceptable salt" is used throughout the specification to describe a salt form of one or more of the compounds herein which are presented to increase the solubility of the compound in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts may be particularly preferred as neutralization salts of carboxylic acid containing compositions according to the present invention. The term "salt" shall mean any salt consistent with the use of the compounds according to the present invention. In the case where the compounds are used in pharmaceutical indications, including the treatment of HIV infections, the term "salt" shall mean a pharmaceutically acceptable salt, consistent with the use of the compounds as pharmaceutical agents.

The term "antibody binding terminal moiety", "antibody binding terminus" or "antibody binding moiety" (ABT within the general formula of compounds according to the present invention) is used to describe that portion of a bifunctional ARM-HI compound according to the present invention which comprises at least one small molecule or hapten which can bind to antibodies within the patient. The term "hapten" is used to describe a small-molecular-weight inorganic or organic molecule that alone is not antigenic but which when linked to another molecule, such as a carrier protein (albumin, etc.) or in the case of the present invention, as an antibody terminus in the present compounds, is antigenic; and an antibody raised against the hapten (generally, the hapten bonded or complexed to the carrier) will react with the hapten alone. Because, in many instances, antihapten (anti-DNP) antibodies are already present in the human blood stream as endogenous antibodies because they naturally become raised to endogenous haptens (already present in patients), no pre-vaccination is necessary for ARM-HI activity.

It is preferred that the antibody binding terminal comprise a hapten which is reactive with (binds to) an endogenous antibody that pre-exists in the patient prior to initiate therapy with the compounds of the present invention and does not have to be separately raised as part of a treatment regimen (for example, by vaccination or other approach for enhancing immunogenicity). Thus, haptens which comprise a di- or trinitro phenyl group as depicted below, or a digalactose hapten (Gal-Gal-Z, preferably Gal-Gal-sugar, preferably Gal-Gal-Glu), are preferred. Additionally, a compound according to the general structure:

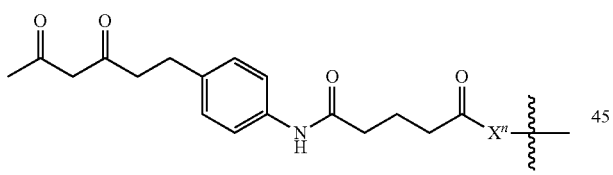

Where $X^n$ is O, $CH_2$, $NR^1$, S; and
$R^1$ is H, a $C_1$-$C_3$ alkyl group or a —C(O)($C_1$-$C_3$) group; May be used as haptens in the present invention.

Further, a moiety according to the chemical structure:

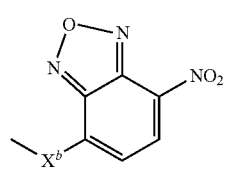

Where $X^b$ is a bond, O, $CH_2$, $NR^1$ or S may also be used as a hapten (ABT) in the present invention.

Other ABT moieties include the following structures:

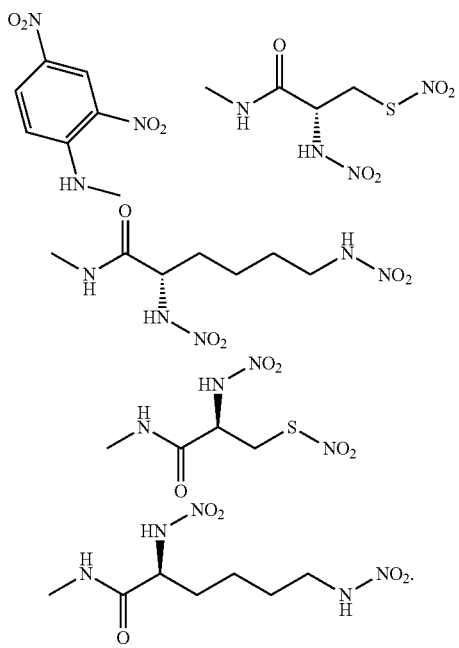

Each of the above amino acid ABT moieties may be further substituted with a dinitrophenyl group through an X group, e.g., $CH_2$—, sulfoxide, sulfone, etc. group as otherwise described herein to provide the following ABT moieties:

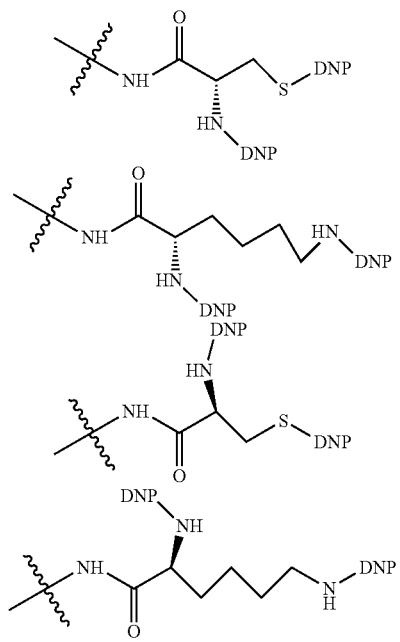

In the above structures in each of the molecules (with the exception of the first, which is DNP amine), DNP may be linked to the structure where the $NO_2$ is linked.

The di- or trinitro phenyl hapten (ABT) moiety for use in the present invention (Dinitropheny or DNP hapten is preferred) may be represented by the following formula:

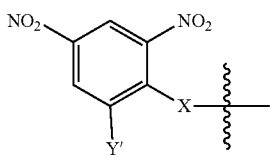

Where Y' is H or NO$_2$ (preferably H);
X is O, CH$_2$, NR$_1$, S(O), S(O)$_2$, —S(O)$_2$O, —OS(O)$_2$, or OS(O)$_2$O; and
R$^1$ is H, a C$_1$-C$_3$ alkyl group, or a —C(O)(C$_1$-C$_3$) group.

The (Gal-Gal-Z) hapten is represented by the chemical formula:

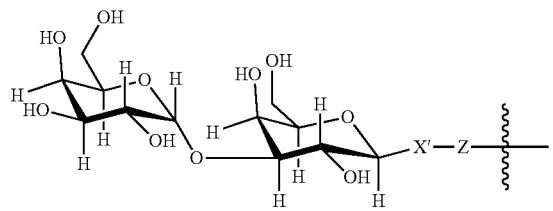

Where X' is CH$_2$, O, N—R$^{1'}$, or S, preferably O;
R$^{1'}$ is H or C$_1$-C$_3$ alkyl; and
Z is a bond, a monosaccharide, disaccharide, oligosaccharide, glycoprotein or glycolipid, preferably a sugar group, more preferably a sugar group selected from the monosaccharides, including aldoses and ketoses, and disaccharides, including those disaccharides described herein. Monosaccharide aldoses include monosaccharides such as aldotriose (D-glyceraldehdye, among others), aldotetroses (D-erythrose and D-Threose, among others), aldopentoses, (D-ribose, D-arabinose, D-xylose, D-lyxose, among others), aldohexoses (D-allose, D-altrose, D-Glucose, D-Mannose, D-gulose, D-idose, D-galactose and D-Talose, among others), and the monosaccharide ketoses include monosaccharides such as ketotriose (dihydroxyacetone, among others), ketotetrose (D-erythrulose, among others), ketopentose (D-ribulose and D-xylulose, among others), ketohexoses (D-Psicone, D-Fructose, D-Sorbose, D-Tagatose, among others), aminosugars, including galactoseamine, sialic acid, N-acetylglucosamine, among others and sulfosugars, including sulfoquinovose, among others. Exemplary disaccharides which find use in the present invention include sucrose (which may have the glucose optionally N-acetylated), lactose (which may have the galactose and/or the glucose optionally N-acetylated), maltose (which may have one or both of the glucose residues optionally N-acetylated), trehalose (which may have one or both of the glucose residues optionally N-acetylated), cellobiose (which may have one or both of the glucose residues optionally N-acetylated), kojibiose (which may have one or both of the glucose residues optionally N-acetylated), nigerose (which may have one or both of the glucose residues optionally N-acetylated), isomaltose (which may have one or both of the glucose residues optionally N-acetylated), β,β-trehalose (which may have one or both of the glucose residues optionally N-acetylated), sophorose (which may have one or both of the glucose residues optionally N-acetylated), laminaribiose (which may have one or both of the glucose residues optionally N-acetylated), gentiobiose (which may have one or both of the glucose residues optionally N-acetylated), turanose (which may have the glucose residue optionally N-acetylated), maltulose (which may have the glucose residue optionally N-acetylated), palatinose (which may have the glucose residue optionally N-acetylated), gentiobiuose (which may have the glucose residue optionally N-acetylated), mannobiose, melibiose (which may have the glucose residue and/or the galactose residue optionally N-acetylated), melibiulose (which may have the galactose residue optionally N-acetylated), rutinose, (which may have the glucose residue optionally N-acetylated), rutinulose and xylobiose, among others. Oligosaccharides for use in the present invention as Z can include any sugar of three or more (up to about 100) individual sugar (saccharide) units as described above (i.e., any one or more saccharide units described above, in any order, especially including glucose and/or galactose units as set forth above), or for example, fructo-oligosaccharides, galactooligosaccharides and mannan-oligosaccharides ranging from three to about ten-fifteen sugar units in size. Glycoproteins for use in the present invention include, for example, N-glycosylated and O-glycosylated glycoproteins, including the mucins, collagens, transferring, ceruloplasmin, major histocompatability complex proteins (MHC), enzymes, lectins and selectins, calnexin, calreticulin, and integrin glycoprotein IIb/IIa, among others. Glycolipids for use in the present invention include, for example, glyceroglycolipids (galactolipids, sulfolipids), glycosphingolipids, such as cerebrosides, galactocerebrosides, glucocerebrosides (including glucobicaranateoets), gangliosides, globosides, sulfatides, glycophosphphingolipids and glycocalyx, among others.

Preferably, Z is a bond (linking a Gal-Gal disaccharide to a linker or connector molecule) or a glucose or glucosamine (especially N-acetylglucosamine).
It is noted that Z is linked to a galactose residue through a hydroxyl group or an amine group on the galactose of Gal-Gal, preferably a hydroxyl group. A preferred hapten is Gal-Gal-Glu which is represented by the structure:

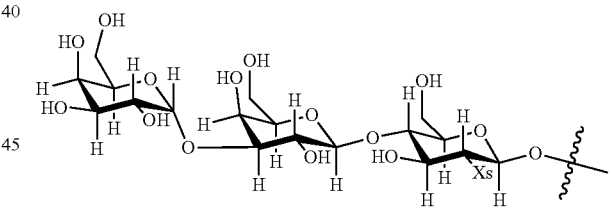

Where Xs is OH or NHAc.
Other ABT groups include, for example, the following groups:

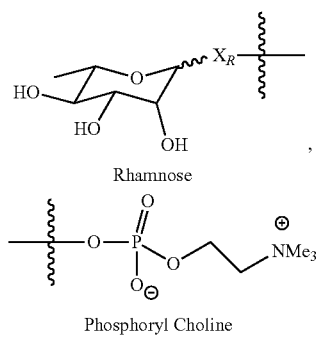

Rhamnose

Phosphoryl Choline

-continued

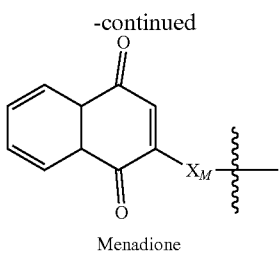

Menadione

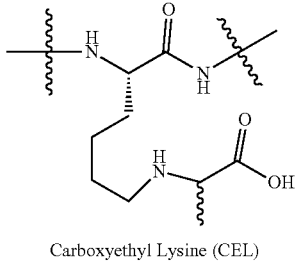

Carboxyethyl Lysine (CEL)

Where $X_R$ is O or S; and
$X_M$ is O or S.

It is noted in the carboxyethyl lysine ABT moiety either one, two or three of the nitrogen groups may be linked to the remaining portion of the molecule through the linker or one or both of the remaining nitrogen groups may be substituted with a dinitrophenyl through an X group as otherwise described herein.

The term "pathogen binding terminus" or "pathogen binding terminal moiety" ("PBT") is use to described that portion of a difunctional ARM-HI compound according to the present invention which comprises at least one small molecule or moiety which can bind specifically to is capable of binding to gp120 envelope protein on HIV virus or a cell surface of CD4 cells which are infected with HIV (HIV+) in said patient.

PBT groups (i.e., the chemical moiety connected to linkers and ABT in the bifunctional chemical compound below) for use in the present invention include those which are found in the following bifunctional compounds having the following chemical structure:

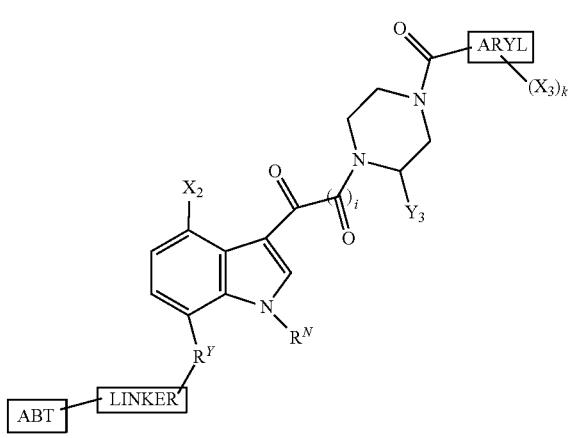

Where

ABT is an antibody binding terminus (moiety) comprising a hapten which is capable of binding to an antibody present in a patient (preferably a DNP group);

LINKER s a linker molecule which chemical links ABT to $R^Y$ or directly to the indole moiety at the carbon atom to which $R^Y$ is attached and which optionally includes a connector CT which may be a bond or a connector molecule;

ARYL is an aromatic or heteroaromatic group, preferably a monocyclic or bicyclic aromatic or heteroaromatic group;

$R^Y$ is absent or is an optionally substituted aryl or heteroaryl group or O, $(CH_2)_j$, $NR^1$, —S—, —NHC(O)—, —NHC(O)NH—, S(O), $S(O)_2$, —$S(O)_2O$, —$OS(O)_2$, or $OS(O)_2O$;

$X_2$ is H, —$(CH_2)_nOH$, —$(CH_2)_nCOOH$, $C_1$-$C_6$ alkyl, —$(CH_2)_nO$—$(C_1$-$C_6$ alkyl), —$(CH_2)_nC(O)$—$(C_1$-$C_6$ alkyl), —$(CH_2)_nNHC(O)$—R, —$(CH_2)_nC(O)$—$NR_1R_2$, —$(CH_2O)_nOH$, —$(CH_2O)_nCOOH$, $C_1$-$C_6$ alkyl, —$(CH_2O)_nO$—$(C_1$-$C_6$ alkyl), —$(CH_2O)_nC(O)$—$(C_1$-$C_6$ alkyl), —$(CH_2O)_nNHC(O)$—$R_1$, —$(CH_2O)_nC(O)$—$NR_1R_2$, $NO_2$, CN or halogen (F, Cl, Br, I preferably F or Cl);

$X_3$ is H, —$(CH_2)_nOH$, —$(CH_2)_nCOOH$, $C_1$-$C_6$ alkyl, —$(CH_2)_nO$—$(C_1$-$C_6$ alkyl), —$(CH_2)_nC(O)$—$(C_1$-$C_6$ alkyl), —$(CH_2)_nNHC(O)$—$R_1$, —$(CH_2)_nC(O)$—$NR_1R_2$, —$(CH_2O)_nOH$, —$(CH_2O)_nCOOH$, $C_1$-$C_6$ alkyl, —$(CH_2O)_nO$—$(C_1$-$C_6$ alkyl), —$(CH_2O)_nC(O)$—$(C_1$-$C_6$ alkyl), —$(CH_2O)_nNHC(O)$—$R_1$, —$(CH_2O)_nC(O)$—$NR_1R_2$, $NO_2$, CN, halogen (F, Cl, Br, I, preferably F or Cl) or a monocyclic aryl or heteroaryl group which itself is optionally substituted;

$R^1$ is H or a $C_1$-$C_3$ alkyl group;

$R_1$ and $R_2$ are each independently H or a $C_1$-$C_6$ alkyl group;

i is 0 or 1, preferably 1;

j is 1, 2 or 3;

k is 0, 1, 2 or 3, preferably 0, 1 or 2;

n is 0, 1, 2, 3, 4, 5, 6, preferably 0-3;

$Y_3$ is H or a $C_1$-$C_3$ alkyl group (preferably, disposed out of or into the plane, preferably out of the plane on the chiral carbon; and $R_N$ is H or a $C_1$-$C_3$ alkyl group which is optionally substituted with one or two hydroxyl groups or up to three halogen groups (preferably F)

or a pharmaceutically acceptable salt, enantiomer, solvate or polymorph thereof.

Preferred PBT groups for use in the present invention include those (i.e., the chemical moiety connected to the linker and ABT below—connected to X) according to the chemical formula:

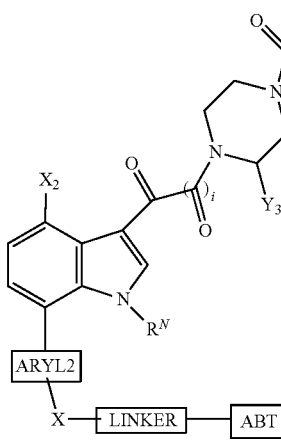

Where

ARYL1 is a monocyclic or bicyclic aryl or heteroary group according to the chemical structure:

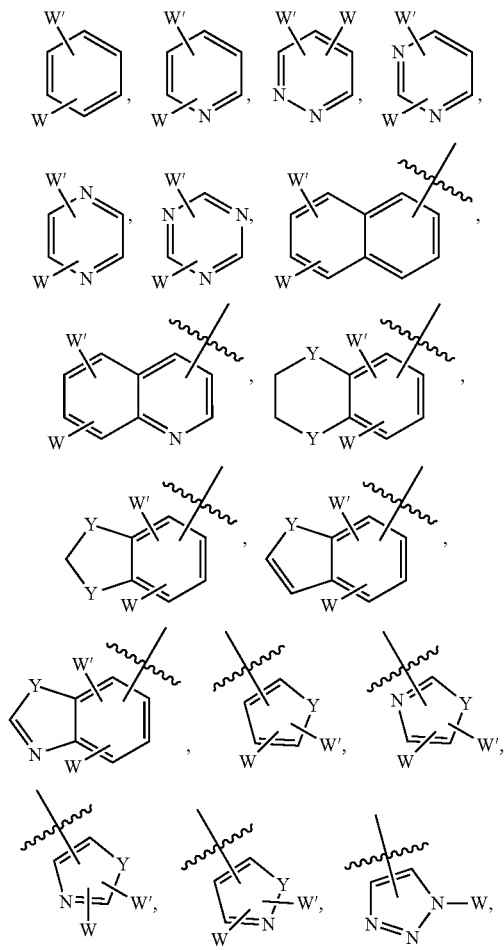

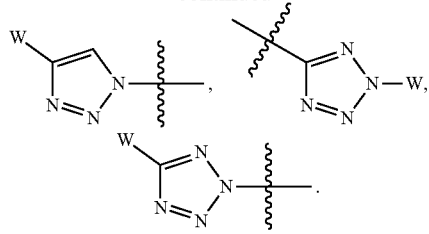

Where W is H, —$(CH_2)_nOH$, —$(CH_2)_nCOOH$, $C_1$-$C_6$ alkyl, —$(CH_2)_nO$—$(C_1$-$C_6$ alkyl), —$(CH_2)_nC(O)$—$(C_1$-$C_6$ alkyl), —$(CH_2)_nNHC(O)$—$R_1$, —$(CH_2)_nC(O)$—$NR_1R_2$, —$(CH_2O)_nOH$, —$(CH_2O)_nCOOH$, $C_1$-$C_6$ alkyl, —$(CH_2O)_nO$—$(C_1$-$C_6$ alkyl), —$(CH_2O)_nC(O)$—$(C_1$-$C_6$ alkyl), —$(CH_2O)_nNHC(O)$—$R_1$, —$(CH_2O)_nC(O)$—$NR_1R_2$, $NO_2$, CN, halogen (F, Cl, Br, I, preferably F or Cl) or a monocyclic aryl or heteroaryl group which itself is optionally substituted (especially an optionally substituted benzoyl or benzyl group);

W' is H, —$(CH_2)_nOH$, —$(CH_2)_nCOOH$, $C_1$-$C_6$ alkyl, —$(CH_2)_nO$—$(C_1$-$C_6$ alkyl) or halogen (preferably F or Cl);

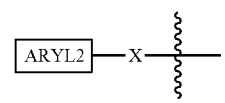

is group according to chemical structure:

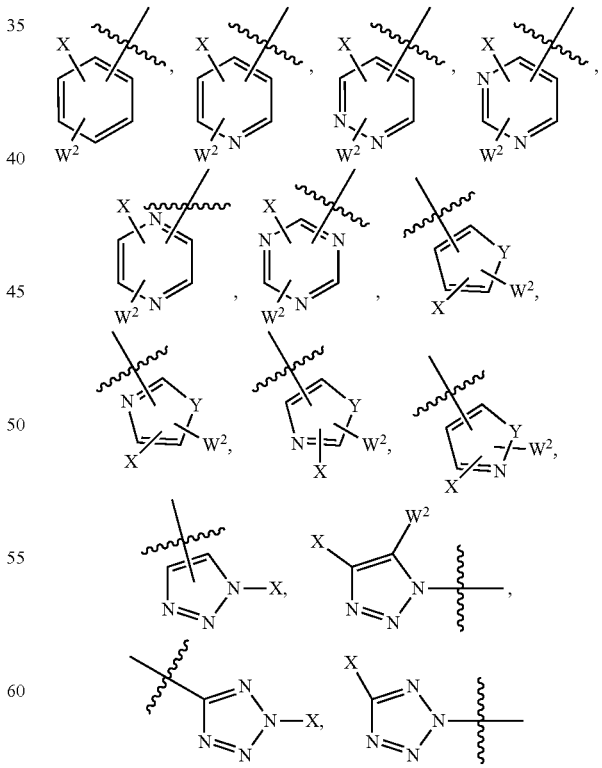

Where $W^2$ is H, —$(CH_2)_nOH$, —$(CH_2)_nCOOH$, $C_1$-$C_6$ alkyl, —$(CH_2)_nO$—$(C_1$-$C_6$ alkyl), —$(CH_2)_nC(O)$—$(C_1$-$C_6$ alkyl), —$(CH_2)_nNHC(O)$—$R_1$, —$(CH_2)_nC(O)$—$NR_1R_2$, —$(CH_2O)_n$OH, —$(CH_2O)_n$COOH, $C_1$-$C_6$ alkyl, —$(CH_2O)_n$O—($C_1$-$C_6$ alkyl), —$(CH_2O)_n$C(O)—($C_1$-$C_6$ alkyl), —$(CH_2O)_n$NHC(O)—R, —$(CH_2O)_n$C(O)—$NR_1R_2$, $NO_2$, CN or halogen (preferably F or Cl);

X is a group $(CH_2)_n$NH—, —$(CH_2)_n$NHC(O), $(CH_2)_n$O, $(CH_2)_m$, $(CH_2)_n$S—, —$(CH_2)_n$S(O)—, —$(CH_2)_n$ $SO_2$— or —$(CH_2)_n$NH—C(O)—NH— which links

ARYL2 to the linker;

Y is O, S or N—R where R is H or a $C_1$-$C_3$ alkyl group;

$X_2$ is H, —$(CH_2)_n$OH, —$(CH_2)_n$COOH, $C_1$-$C_6$ alkyl, —$(CH_2)_n$O—($C_1$-$C_6$ alkyl), —$(CH_2)_n$C(O)—($C_1$-$C_6$ alkyl), —$(CH_2)_n$NHC(O)—$R_1$, —$(CH_2)_n$C(O)—$NR_1R_2$, —$(CH_2)_n$OH, —$(CH_2O)_n$COOH, $C_1$-$C_6$ alkyl, —$(CH_2O)_n$O—($C_1$-$C_6$ alkyl), —$(CH_2O)_n$C(O)—($C_1$-$C_6$ alkyl), —$(CH_2O)_n$NHC(O)—$R_1$ or —$(CH_2O)_n$C(O)—$NR_1R_2$, $NO_2$;

$R_1$ and $R_2$ are each independently H or a $C_1$-$C_6$ alkyl group;

$Y_3$ is H or a $C_1$-$C_3$ alkyl group (preferably, disposed out of or into the plane, preferably out of the plane on the chiral carbon; and $R^N$ is H or a $C_1$-$C_3$ alkyl group which is optionally substituted with one or two hydroxyl groups or up to three halogen groups (preferably F);

i is 0 or 1, preferably 1; and m is 1, 2, 3, 4 or 5, preferably 1, 2 or 3, more preferably 1; and Each n is independently 0, 1, 2 or 3, or a pharmaceutically acceptable salt, enantiomer, solvate or polymorph thereof.

The term "linker" refers to a chemical entity connecting an antibody binding terminus (ABT) moiety to a pathogen binding terminus (CBT) moiety, optionally through a connector moiety (CT) through covalent bonds. The linker between the two active portions of the molecule, that is the antibody binding terminus (ABT) and the pathogen binding terminus (PBT) ranges from about 5 Å to about 50 Å or more in length, about 6 Å to about 45 Å in length, about 7 Å to about 40 Å in length, about 8 Å to about 35 Å in length, about 9 Å to about 30 Å in length, about 10 Å to about 25 Å in length, about 7 Å to about 20 Å in length, about 5 Å to about 16 Å in length, about 5 Å to about 15 Å in length, about 6 Å to about 14 Å in length, about 10 Å to about 20 Å in length, about 11 Å to about 25 Å in length, etc. Linkers which are based upon ethylene glycol units and are between 4 and 14 glycol units in length may be preferred. By having a linker with a length as otherwise disclosed herein, the ABT moiety and the PBT moiety may be situated to advantageously take advantage of the biological activity of compounds according to the present invention which bind to HIV envelope protein gp120 (gp120) and attract endogenous antibodies to the virus and/or infected cells (e.g. HIV infected CD4 cells) to which the compounds are bound, resulting in the selective and targeted death of those viruses and/or cells. The selection of a linker component is based on its documented properties of biocompatibility, solubility in aqueous and organic media, and low immunogenicity/antigenicity. Although numerous linkers may be used as otherwise described herein, a linker based upon polyethyleneglycol (PEG) linkages, polypropylene glycol linkages, or polyethyleneglycol-co-polypropylene oligomers (up to about 100 units, about 1 to 100, about 1 to 75, about 1 to 60, about 1 to 50, about 1 to 35, about 1 to 25, about 1 to 20, about 1 to 15, 2 to 10, about 4 to 12, about 1 to 8, 1 to 3, 1 to 4, 2 to 6, 1 to 5, etc.) may be favored as a linker because of the chemical and biological characteristics of these molecules. The use of polyethylene (PEG) linkages is preferred. Alternative preferred linkers may include, for example, polyproline linkers and/or collagen linkers as depicted below (n is about 1 to 100, about 1 to 75, about 1 to 60, about 1 to 50, about 1 to 45, about 1 to 35, about 1 to 25, about 1 to 20, about 1 to 15, 2 to 10, about 4 to 12, about 5 to 10, about 4 to 6, about 1 to 8, about 1 to 6, about 1 to 5, about 1 to 4, about 1 to 3, etc.).

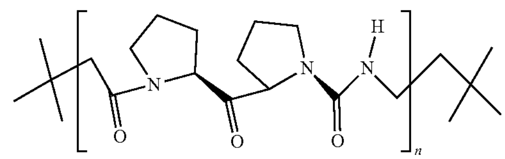

or polyproline linker 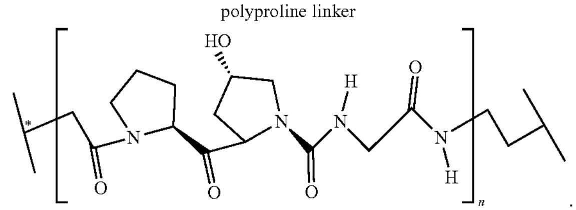 collagen linker

Preferred linkers include those according to the chemical structures:

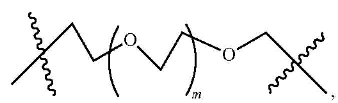

, 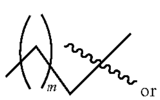 or

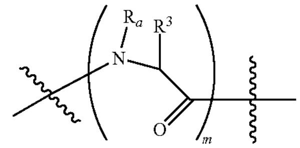

Or a polypropylene glycol or polypropylene-co-polyethylene glycol linker having between 1 and 100 glycol units;

Where $R_a$ is H, $C_1$-$C_3$ alkyl or alkanol or forms a cyclic ring with $R^3$ (proline) and $R^3$ is a side chain derived from an amino acid preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline ($R^3$ forms a cyclic ring with $R^3$ and the adjacent nitrogen group to form a pyrrolidine group), hydroxyproline, serine (methanol), threonine (ethanol, 1-hydroxyethane), tryptophan (methyleneindole), tyrosine (methylene phenol) or valine (isopropyl);

m (within this context) is an integer from 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

n (within this context) is an integer from about 1 to 100, about 1 to 75, about 1 to 60, about 1 to 50, about 1 to 45, about 1 to 35, about 1 to 25, about 1 to 20, about 1 to 15, 2 to 10, about 4 to 12, about 5 to 10, about 4 to 6, about 1 to 8, about 1 to 6, about 1 to 5, about 1 to 4, about 1 to 3, etc.) or Another linker according to the present invention comprises a polyethylene glycol linker containing from 1 to 1 to 100, 1 to 75, 1 to 60, 1 to 55, 1 to 50, 1 to 45, 1 to 40, 2 to 35, 3 to 30, 1 to 15, 1 to 10, 1 to 8, t o 6, 1, 2, 3, 4 or 5 ethylene glycol units, to which is bonded a lysine group (preferably at its carboxylic acid moiety) which binds one or two DNP groups to the lysine at the amino group(s) of lysine. Still other linkers comprise amino acid residues (D or L) to which are bonded to ABT moieties, in particular, DNP, among others at various places on amino acid residue as otherwise described herein. In another embodiment, as otherwise described herein, the amino acid has anywhere from 1-15 methylene groups separating the amino group from the acid group in providing a linker to the ABT moiety.

Or another linker is according to the chemical formula:

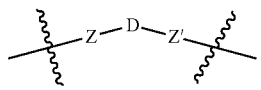

Where Z and Z' are each independently a bond, —(CH$_2$)$_i$—O, —(CH$_2$)$_i$—S, —(CH$_2$)$_i$—N—R,

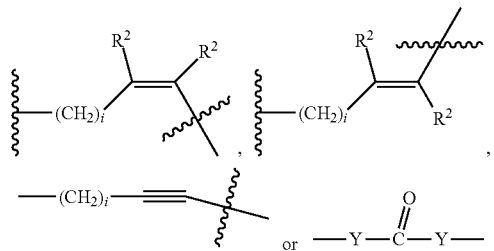

wherein said —(CH$_2$)$_i$ group, if present in Z or Z', is bonded to a connector, ABT or CBT;

Each R is H, or a C$_1$-C$_3$ alkyl or alkanol group;

Each R$^2$ is independently H or a C$_1$-C$_3$ alkyl group;

Each Y is independently a bond, O, S or N—R;

Each i is independently 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5; D is

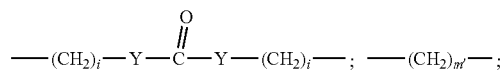

or a bond, with the proviso that Z, Z' and D are not each simultaneously bonds;

j is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

m' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

n is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

X$^1$ is O, S or N—R; and

R is as described above, or a pharmaceutical salt thereof.

The term "connector", symbolized in the generic formulas by [CT], is used to describe a chemical moiety which is optionally included in bifunctional compounds according to the present invention which forms from the reaction product of an activated ABT-linker with a PTB moiety (which also is preferably activated) or an ABT moiety with an activated linker-PTB as otherwise described herein. The connector group is often the resulting moiety which forms from the facile condensation of two or more separate chemical fragments which contain reactive groups which can provide connector groups as otherwise described to produce bifunctional or multifunctional compounds according to the present invention. It is noted that a connector may be distinguishable from a linker in that the connector is the result of a specific chemistry which is used to provide bifunctional compounds according to the present invention wherein the reaction product of these groups results in an identifiable connector group or part of a connector group which is distinguishable from the linker group, although in certain instances, incorporated into the linker group, as otherwise described herein. It is noted also that a connector group may be linked to a number of linkers to provide multifunctionality (i.e., more than one PBT moiety and/or more than one ABT moiety within the same molecule. It is noted that there may be some overlap between the description of the connector group and the linker group such that the connector group is actually incorporated or forms part of the linker, especially with respect to more common connector groups such as amide groups, oxygen (ether), sulfur (thioether) or amine linkages, urea or carbonate —OC(O)O— groups as otherwise described herein. It is further noted that a connector (or linker) may be connected to ABT, a linker or PBT at positions which are represented as being linked to another group using the using the symbol

Where two or more such groups are present in a linker or connector, any of an ABT, a linker or a PBT may be bonded to such a group. Where that symbol is not used, the link may be at one or more positions of a moiety.

Common connector groups which are used in the present invention include the following chemical groups:

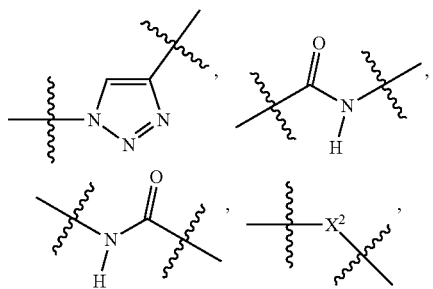

-continued

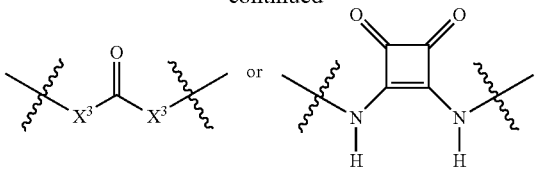

or

Where $X^2$ is O, S, $NR_4$, S(O), $S(O)_2$, —$S(O)_2O$, —$OS(O)_2$, or $OS(O)_2O$;

$X^3$ is O, S, $NR^4$; and $R^4$ is H, a $C_1$-$C_3$ alkyl or alkanol group, or a —$C(O)(C_1$-$C_3)$ group. The triazole group, indicated above, is a preferred connector group.

It was shown in international application PCT/US2010/52344 (published as WO/2011/046946), which is incorporated by reference herein, that it was possible to derivatize Formula 1, at the carbon atom of the C4 methoxy group, in which the carbon atom of the C4 methoxy group could be replaced with various bulky substituents, (Wang, J, S.; Le, N.; Heredia, A.: Song, H. J.: Redfield, R.: Wang, L. X. Org. Biomol. Chem. 2005, 3, 1781-1786) so as to provide a linker which would attract DNP without sacrificing the compound's ability to inhibit viral entry. This hypothesis was supported by an analysis of a published computational docking model suggesting that the C4 methoxy group in Formula 1 points toward the solvent in the complex. See Kong. R.; Tan, J.; Ma, X.; Chen, W.; Wang. C:. Biochim. Biophys. Acta 2006, 1764. 766-7728.

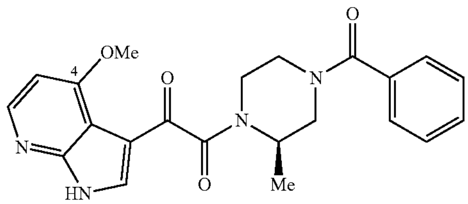

(1)

BMS-378806

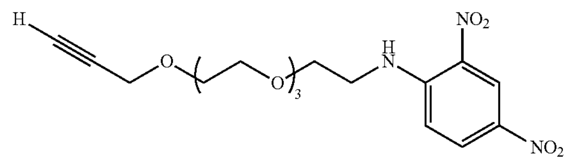

2

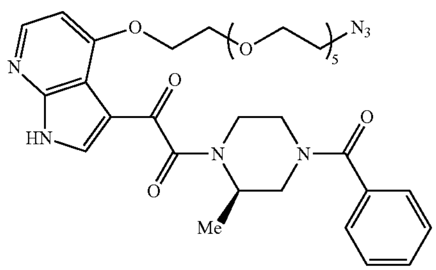

3

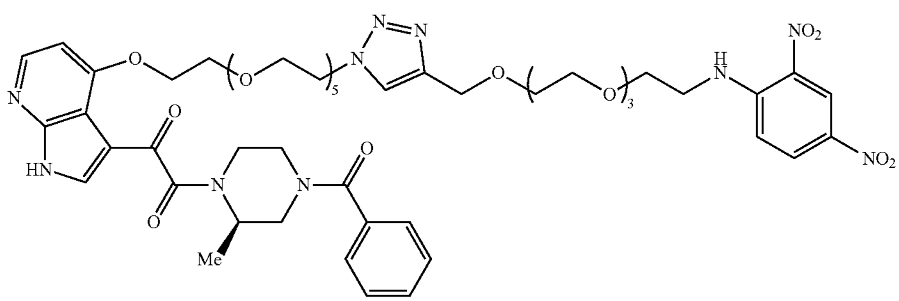

4

(ARM-H)

As discussed hereinabove, it is noted that each of the above groups may be further linked to a chemical moiety which bonds two or more of the above connector groups into a multifunctional connector, thus providing complex multifunctional compounds comprising more than one ABT and/or PBT group within the multifunctional compound.

Initial work by the inventors involved in identifying bifunctional compounds ARM-HI according to the present invention, began with the small molecule BMS-378806 (Formula 1, below), (4-benzoyl-1-(2-(4-methoxy-1H-pyrrolo(2,3-b) pyridin-3-yl)-1,2-dioxoethyl)-2-methyl-, (2R)-Piperazine, CAS Number 357263-13-9, MW 406), a known inhibitor of the CD4-gp120 interaction. (Wang, et al. J. Med. Chem. 2003, 46, 4236-42396).

Thus, in accordance with the invention of PCT/US2010/52344 (published as WO/2011/046946), Formula 1 was re-engineered to include the capability to recruit anti-DNP antibodies to gp120-expressing particles (infected cells or viruses), increasing the "visibility" of the combination to the human immune system. Consequently, an ARM-HI of Formula 4 was prepared in high yield (38% overall) via azide-alkyne cycloaddition (Rostovtsev, V. V.; Green, L. G.; Fokin, V. V.; Sharpless, K. B. Angew. Chem., 1nt, Ed. 2002, 41, 2596-2599. Tornoe, C.; Christensen, C.; Meldal, M. J. Org. Chem. 2002, 67, 3057-3064) of the compounds of Formula 2 and Formula 3, which were derived in turn from known intermediates. See, Wang, T.; et al. J. Med. Chem. 2003, 46, 4236-4239.

As discussed above, ARM-HI compounds, including compounds according to the present invention, target HIV by inhibiting virus entry while targeting Env-expressing cells for immune recognition and clearance. (See FIG. 1) Compounds set forth in the prior PCT application were shown to inhibit CD4 binding to HIV-1 gp120 and to out-compete the CD4-gp120 interaction. It was confirmed that ARM-HI has the ability to recruit antibodies to gp120 both in vitro and in tissue culture. Initial ELISA experiments demonstrated a concentration-dependent increase in anti-DNP antibody binding to the ARM-HI-gp120 complex but not to gp120 alone. Thus, ARM-HI is capable of templating a ternary complex that also includes gp120 and anti-DNP antibody.

It was also confirmed that the ternary association could form in a complex cellular milieu, and that ARM-H bifunctional compounds have the ability to recruit anti-DNP antibodies to HIV-Env-expressing Chinese hamster ovary cells (CHO-gp120 cells). Thus, the previous results presented in PCT/US2010/52344 (published as WO/2011/046946) provide strong evidence that ARM-HI bifunctional agents of the present invention are capable of recruiting anti-hapten (e.g. anti-DNP) antibodies to cells expressing the Env glycoprotein in a fashion that depends upon its simultaneous binding to both gp120 and anti-DNP antibodies and that the ternary complex formed from anti-DNP antibody, ARM-HI, and alive Env-expressing cell activates complement proteins and mediates cellular death.

Notably, in the absence of anti-DNP antibody and complement-preserved serum (data in green), in cells lacking the Env glycoprotein(CHO-WT, data in black), or in the presence of compound which lacks the DNP group, no cell death is observed, suggesting that termolecular complex formation is necessary for complement-dependent cytotoxicity (CDC) and that ARM-HI itself is not toxic to cells.

The present invention takes a novel approach and is directed to the development of further novel compositions which recruit anti-DNP antibodies and other anti-hapten antibodies, endogenous in most patients, to HIV via binding to the gp120 envelope protein, which additionally prevents HIV from binding to CD4 and T4 cells, providing novel compositions and therapy for treating HIV infection and the symptoms associated therewith. The present compounds exhibit substantially greater activity than the compounds which are disclosed in PCT/US2010/52344 (published as WO/2011/046946).

The following detailed description outlines the design and synthesis of a number of bifunctional small-molecules capable of redirecting endogenous anti-hapten antibodies, especially including anti-dinitrophenyl (DNP) antibodies selectively to HIV, and inducing antibody-directed, cell-mediated cytotoxicity, which are based upon the results obtained for the compounds originally presented in PCT/US2010/52344 (WO/2011/046946).

Figure 3:
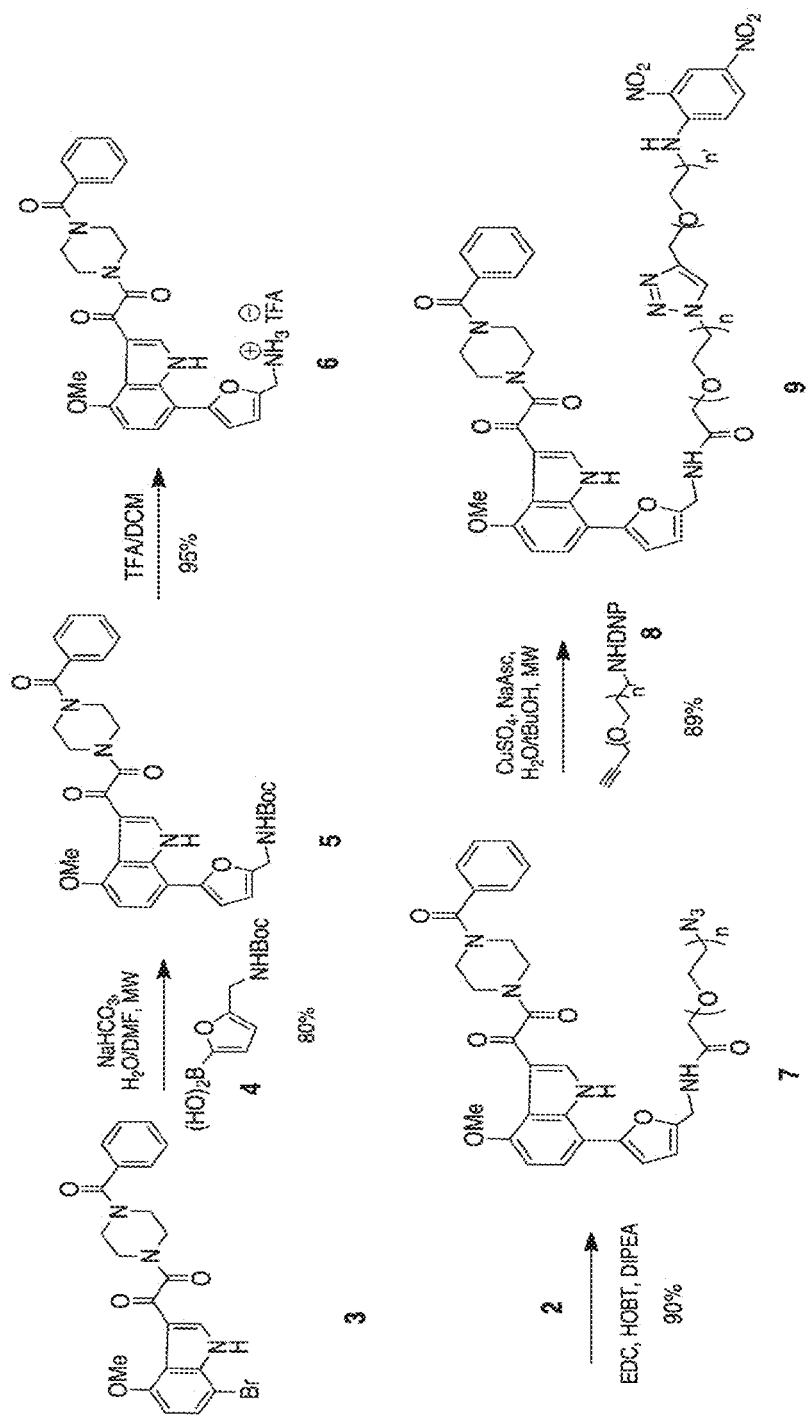
FIG. 3 shows Scheme 1, providing the synthesis of compound 2, presented in the examples of the present application.
Figure 4:
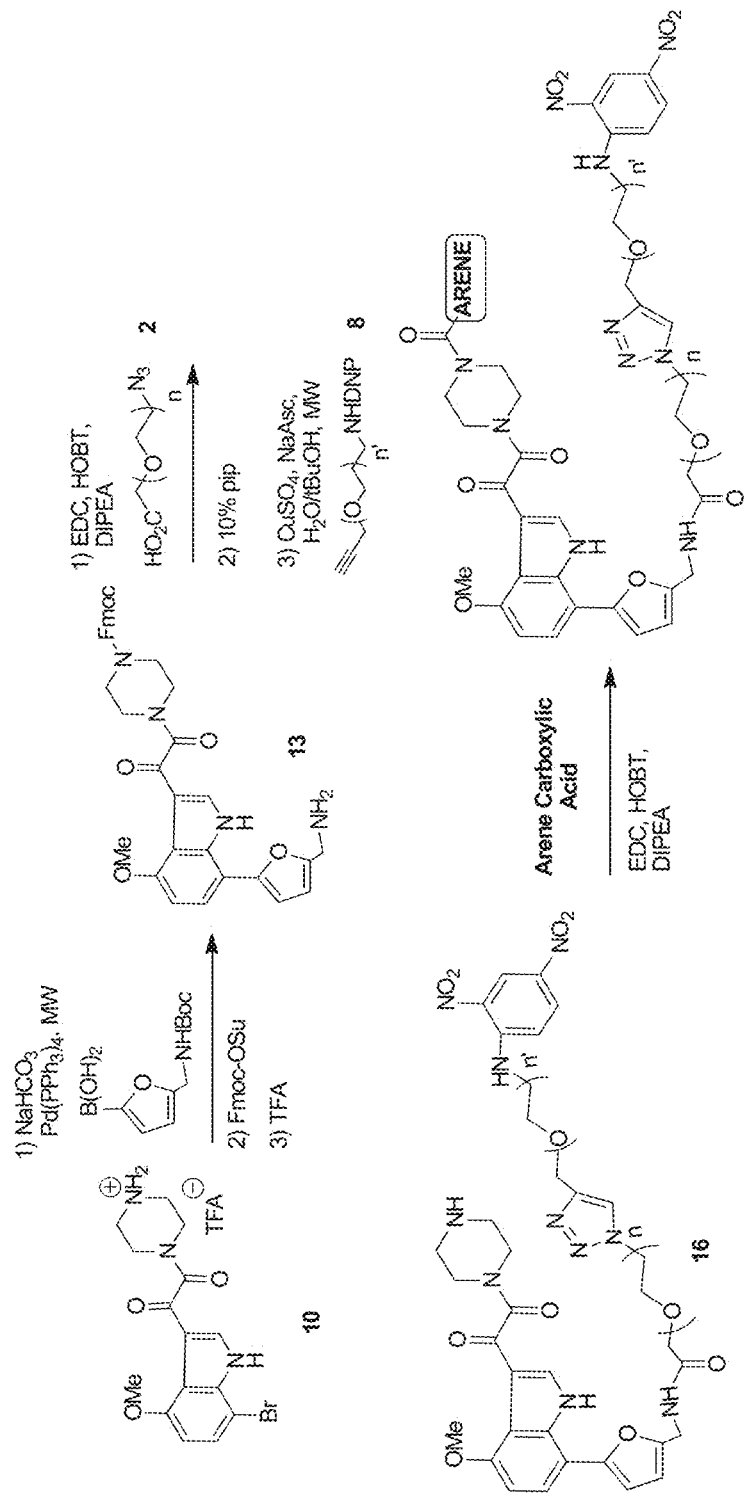
FIG. 4 shows Scheme 2, providing the synthesis of compound 9, presented in the examples of the present application.
Figure 5:
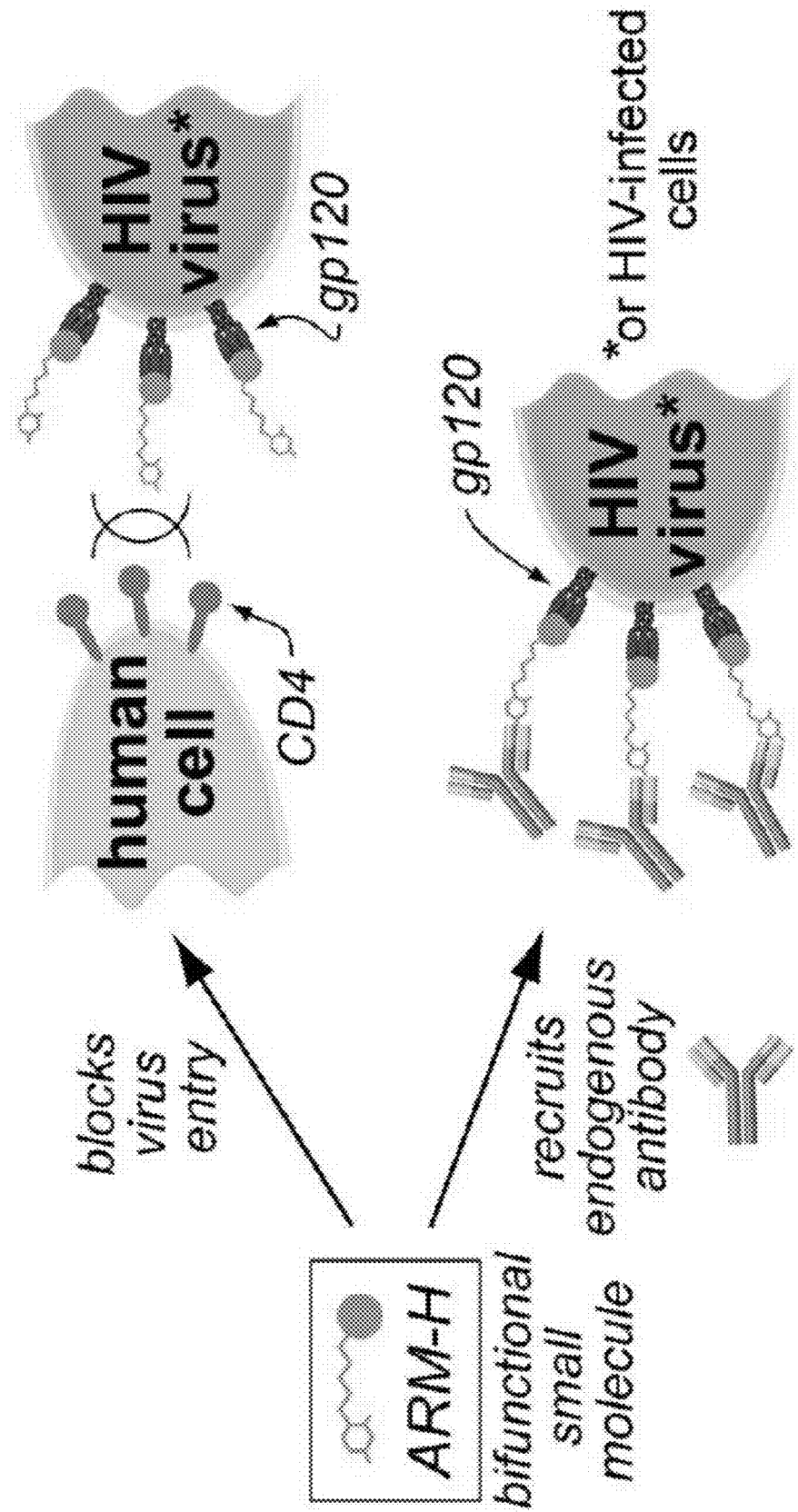
FIG. 5 shows Scheme 3, which provides for the general synthetic route to analogous compounds according to the present invention.
Figure 6:
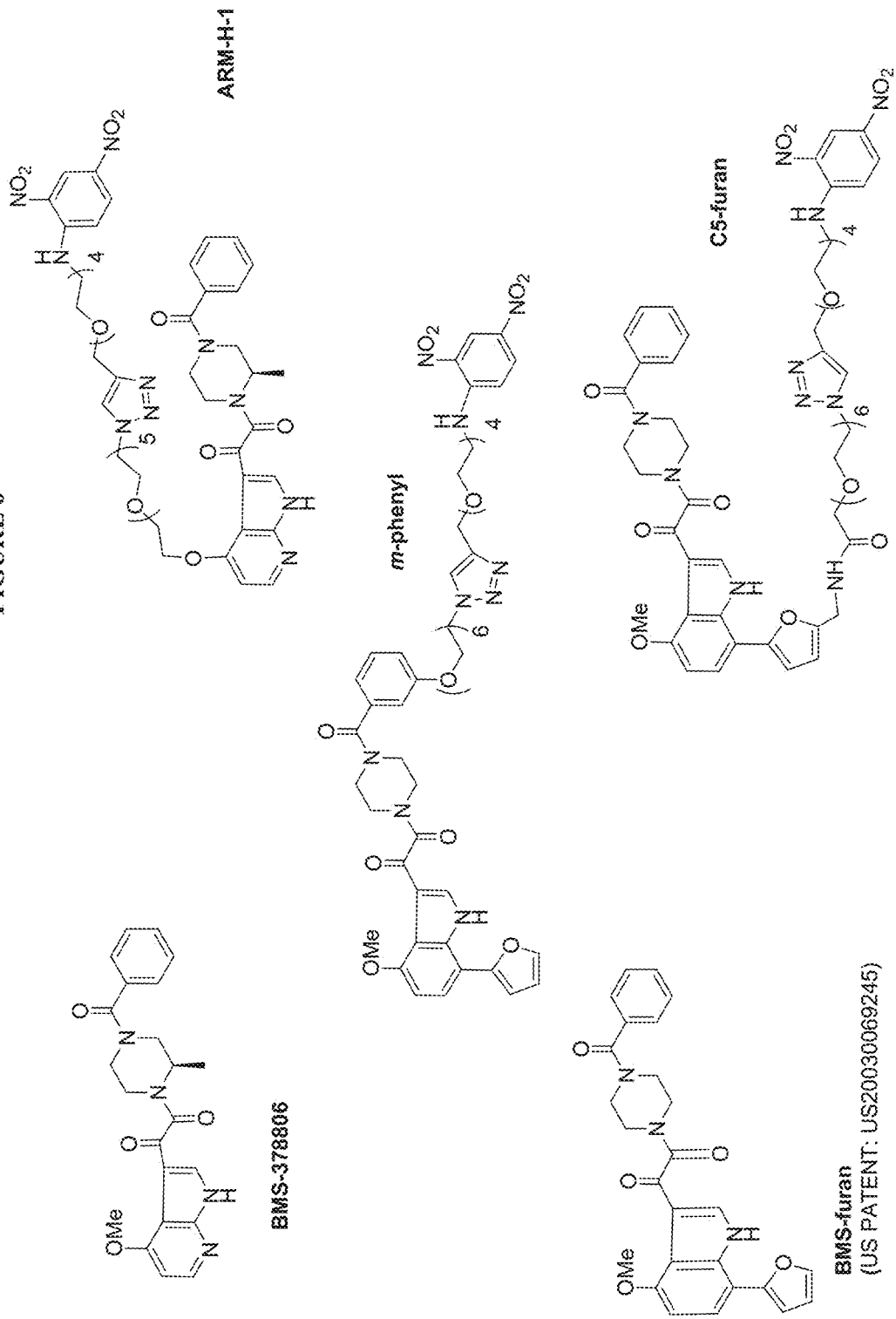
FIG. 6 shows the four compounds which were tested in a viral inhibition assay and compared to the inhibition in the same assay of a bifunctional compound (C5-furan) according to the present invention, also presented in FIG. 6.

The following chemical synthesis which is presented in Scheme 1 (FIG. 3) and Scheme 2 (FIG. 4) may be used to synthesize the compound labeled as C-5 Furan in FIG. 6 which shows exceptional activity as an anti-HIV agent. The Scheme 1 and Scheme 2 chemical syntheses are genericized in Scheme 3, FIG. 5, to provide generic methods (either directly or by analogy) for producing virtually all of the compounds which are described herein.

By way of synthesis, the carboxylic acid azide compound 2 (the azide readily forming a triazole connector molecule with an acetylenic group which links the ABT group with the PBT group) is prepared as otherwise described herein. Pursuant to scheme 1, FIG. 3, the oligo(ethylene oxide) azide compound 1 is modified in sodium hydride and solvent (THF) with bromoacetic acid to provide compound 2, which contains both an electrophilic moiety (the carboxy group can condense to form an amide with an amine group) and an azide which can react with an acetylenic group to form a triazole (connector group).

The pathogen binding terminus (PBT) group in the present application is modified to contain an aryl group (ARYL2) on carbocyclic group of the indole bicyclic ring. Scheme 2 (FIG. 4) provides a rather facile synthesis of C-5 furan from the bromo-substituted indole compound 4, which condenses a substituted furan compound (4) onto the indole ring as indicated in Scheme 2 to produce the furan-substituted PTB compound 5. Compound 5 is treated with trifluoroacetic acid in dichloromethane to produce intermediate 6 which is reacted with carboxyl azide compound 2 to produce compound 7. Compound 7 is then reacted with a compound containing an acetylenic moiety and an ABT group (in Scheme 2, a DNP group) under favorable conditions to produce the active bifunctional compound C5-furan (containing a PBT group containing a furanyl group and an ABT group linked together through a linking group, see FIG. 6).

The chemical synthesis provided above may be presented in a more generalized fashion as set forth in Scheme 3, FIG. 5. In the generic synthesis a bromo-substituted indole compound is first reacted with oxalyl chloride followed by protected piperazine in trifluoroacetic acid to produce compound 10. An aryl group substituting for the bromo group in the indole moiety may be introduced as Arene 1 (Scheme 3, FIG. 5) by reacting an aryl hydroxy boron substituted compound containing an alkylene group substituted with a hydroxyl, an amine or a sulfhydryl group which provides compound 11, which may be further reacted with carboxylic acid azide compound 2 to form an azide containing compound which is then further reacted with an acetylene containing group (containing a linker group and a ABT group (DNP) to condense the acetylenic group onto the azide to form a triazole containing compound 13. Compound 13 may be further reacted with an appropriately substituted (carboxylic acid group which can be condensed onto free amine group of the piperazine moiety) aryl group (arene 2, FIG. 5) to form the final bioactive biofunctional compounds according to the present invention. As noted, this generic synthesis may be used to provide a larger number of compounds which can accommodate numerous aryl groups and numerous ABT groups as indicated. Various analogs are also synthesized, specifically exemplary compounds of the invention which include alternative ABT substituents. Combing an ABT group (with or without a further linking group) containing an acetylenic group with an azide is rather facile and the formation of an azide group and/or an acetylenic group may be used to generally link the ABT group to the PBT group through a connector/linker as otherwise described herein.

Thusly, in the present invention a PBT portion of a molecule is derivatized with a linker containing an azide group which can form a connector molecule in subsequent reactions. Once the derivative PBT molecule is formed, bifunctional compounds according to the present invention may be formed by condensation with appropriate ABT-containing molecules to produce the final bifunctional compounds according to the present invention.

Using the above synthesis with appropriate modification, bifunctional compounds according to the present invention may be readily synthesized. These compounds contain a single PBT moiety to which is linked a compound comprising an ABT moiety.

The above schemes provide exemplary synthesis of compounds according to the present invention with various iterations of same provided by analogy using well known methods as described herein and as understood by those of ordinary skill in the art. It is noted that the experimental section provides significant detail to allow the facile synthesis of a variety of bifunctional compounds as otherwise described herein. The schemes are not to be considered limiting in setting forth teachings which provide compounds according to the present invention.

Turning to the biological data of bifunctional compounds according to the present invention, with reference to FIG. 6, this figure shows a number of compounds which were tested in a viral inhibition assay. In this assay, $IC_{50}$'s of a number of prior art compounds were determined against different HIV-1 isolates as set forth in Table 1 below. In this assay, viral inhibition was determined by HIV Tat-induced luciferase (Luc) reporter gene expression after a single round of virus infection in TZM-bl cells according to the method of Platt, et al., *J Virol.* 1998, 72, 2855-64. This biological data evidences that the present compounds are unexpectedly more active than are the compounds having a linker and ABT moiety at different positions of the indole ring, an unexpected result.

| Compound Figure 6 | JR-FL | ADA | HXBc2 | SF162 | BaL |
|---|---|---|---|---|---|
| BMS-378806 | 2595 | 344 | 31.9 | 359 | dnc |
| ARM-HI1 | 290 | 1003 | dnc | Dnc | dnc |
| BMS-furan | 0.117 | 0.152 | 0.097 | 0.005 | 0.01 |
| m-phenyl | 52.8 | 375 | 208 | 20800 | 150257 |
| C5-furan (Present Invention) | 0.720 | 6.35 | 10.3 | 309 | 34.8 |

*Note
All values in nM;
dnc = does not converge

While specific analogs have been shown and described, the present invention is not limited to these specific analogs and other antibody recruiting compounds that can function as the antibody recruiting terminus connected by a linker to a binding terminus that will bind to the HIV glycoprotein gp120 (gp120 on the viral membrane as well as gp120 displayed on infected cells), would fall within the scope of the present invention. All of these compounds can be formulated into pharmaceutical compositions as otherwise described herein and used in the methods which are presented.

Pharmaceutical compositions comprising combinations of an effective amount of at least one bifunctional compound according to the present invention, and one or more of the compounds otherwise described herein, all in effective amounts, in combination with a pharmaceutically effective amount of a carrier, additive or excipient, represents a further aspect of the present invention.

The compositions of the present invention may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. In certain preferred aspects of the invention, the topical cream or lotion may be used prophylatically to prevent infection when applied topically in areas prone toward virus infection. In additional aspects, the compounds according to the present invention may be coated onto the inner surface of a condom and utilized to reduce the likelihood of infection during sexual activity.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other bifunctional compound according to the present invention or other anti-HIV agent which may be used to treat HIV infection or a secondary effect or condition thereof.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject (e.g. a male human) suffering from HIV infection can be treated by administering to the patient (subject) an effective amount of the ARM-HI compound according to the present invention including pharmaceutically acceptable salts, solvates or polymorphs, thereof optionally in a pharmaceutically acceptable carrier or diluent, either alone, or in combination with other known antiviral or pharmaceutical agents, preferably agents which can assist in treating HIV infection, including AIDS or ameliorate the secondary effects and conditions associated with HIV infection. This treatment can also be administered in conjunction with other conventional HIV therapies.

These compounds can be administered by any appropriate route, for example, orally, parenterally, intravenously, intradermally, subcutaneously, or topically, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 µM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as other anti-HIV agents, antibiotics, antifungals, anti-inflammatories, or anti-viral compounds. In certain preferred aspects of the invention, one or more ARM-HI compounds according to the present invention are coadministered with another anti-HIV agent and/or another bioactive agent, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Detailed Synthetic Information
Materials and General Information:

Purchased starting materials were used as received unless otherwise noted. All moisture sensitive reactions were performed in an inert, dry atmosphere of nitrogen in flame dried glassware. Reagent grade solvents were used for extractions and flash chromatography. Reaction progress was checked by analytical thin-layer chromatography (TLC, Merck silica gel 60 F-254 plates). The plates were monitored either with UV illumination, or by charring with anisaldehyde (2.5% p-anisaldehyde, 1% AcOH, 3.5% $H_2SO_4$(conc.) in 95% EtOH) or ninhydrin (0.3% ninhydrin (w/v), 97:3 EtOH-AcOH) stains. Flash column chromatography was performed using silica gel (230-400 mesh). The solvent compositions reported for all chromatographic separations are on a volume/volume (v/v) basis. ELISA and CDC experiments were performed in triplicate and repeated at least three times unless otherwise noted. I Instrumentation:

$^1$H-NMR spectra were recorded at either 400 or 500 MHz and are reported in parts per million (ppm) on the δ scale relative to $CDCl_3$ (δ 7.26) as an internal standard unless otherwise noted. Data are reported as follows: chemical shift, multiplicity (s=singlet, d=doublet, t=triplet, q=quartet, br=broad, m=multiplet), coupling constants (Hz), and integration. $^{13}$C-NMR spectra were recorded at either 100 or 125 MHz and are reported in parts per million (ppm) on the δ scale relative to $CDCl_3$ (δ 77.00). High resolution mass spectra (HRMS) were recorded on a 9.4T Bruker Qe FT-ICR MS (W.M. Keck Facility, Yale University). Analytical ultra high-performance liquid chromatography-mass spectrometry (UPLC/MS) was performed on a Waters UPLC/MS instrument equipped with a reverse-phase C18 column (1.7 μm particle size, 2.1×50 mm), dual atmospheric pressure chemical ionization (API)/electrospray (ESI) mass spectrometry detector, and photodiode array detector. Samples were eluted with a linear gradient of 20% acetonitrile-water→100% acetonitrile containing 0.1% formic acid over 3 min at a flow rate of 0.8 mL/min. Analytical UPLC/MS data are represented as follows: m/z; retention time (Rt) in minutes. High Pressure Liquid Chromatography (HPLC) using a Dynamax Rainin Solvent Delivery System equipped with a Varian Prostar Detector (Galaxie Chromatography Data System version 1.8.505.5), and absorbance measurements were made at 214 and 254 nm simultaneously. A Waters Xterra Prep MS C18 7.8×150 mm column was used for semi-preparative purifications using a water:acetonitrile (A:B) gradient containing 0.1% TFA at 5.0 mL/min, as specified below for individual compounds. Analytical HPLC analysis was performed using a Varian C8 4.6×250 mm Microsorb C8 column run at a flow rate of 1.0 mL/min water:acetonitrile (A:B) gradient containing 0.1% TFA. Unless otherwise noted, all micro-plate based assays were quantitated using a BioTek Synergy 3 Microplate reader and data was fitted and graphed using GraphPad Prism version 5.00 for Windows (GraphPad Software, San Diego Calif. USA, www.graphpad.com) or KaleidaGraph (Synergy Software).

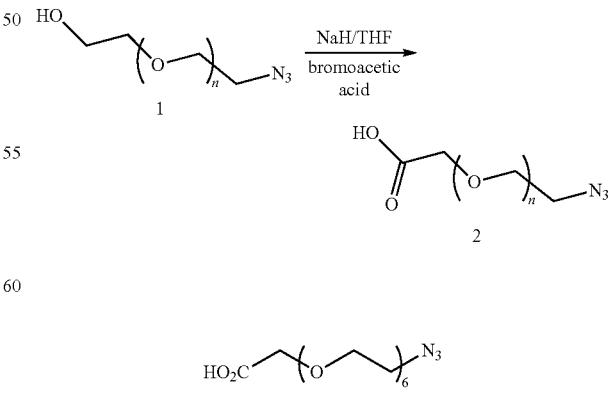

Scheme 1. Synthesis of 2.

Azido polyethylene glycol 6 (0.60 g, 2 mmol, 1 equiv.) was dissolved in dry THF (10 mL) and cooled at 0° C., then sodium hydride (0.15 g, 6.3 mmol, 3.1 equiv.) was added in portions followed by bromoacetic acid (0.35 g, 2.5 mmol, 1,25 equiv.). The suspension was stirred at room temperature under nitrogen overnight. Water (1 mL) was added carefully and then stirred for 5 min. The reaction mixture was concentrated in vacuo. Dichloromethane was added and organic layer was washed with 2N HCl and brine. The organic layer was dried over $Na_2SO_4$ and all solvents were evaporated. Pure 6 (0.72 g, 98%) was obtained as an oil. $^1$H NMR (400 MHz, $CDCl_3$) δ 4.16 (s, 2H), 3.76 (s, 2H), 3.72-3.58 (m, 20H), 3.39 (s, 2H). MS (ES+) 366 [M+H]$^+$, 338 [M+H-$N_2$]

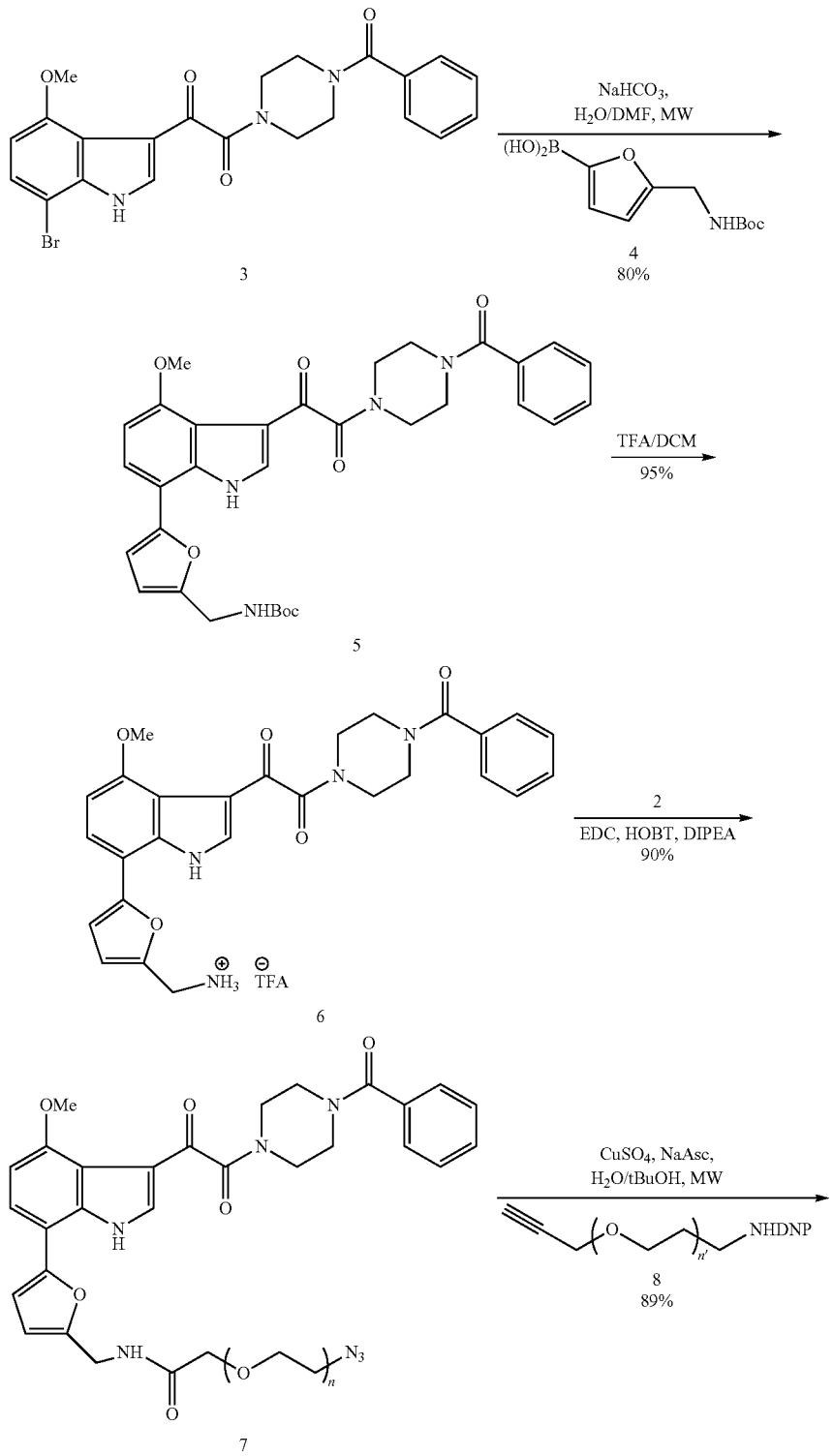

Scheme 2. Synthesis of 9 from known 3.

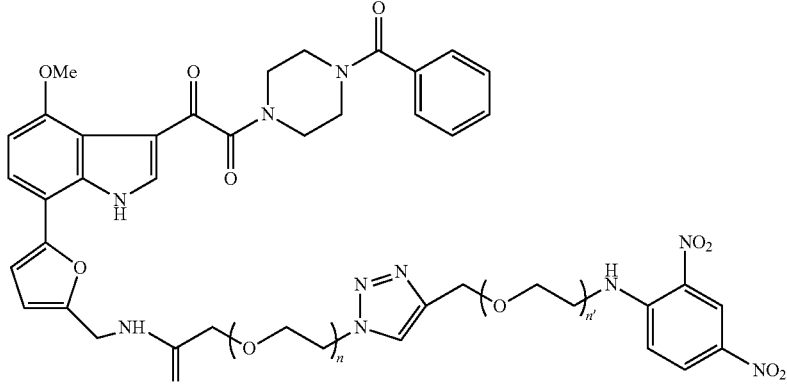

9

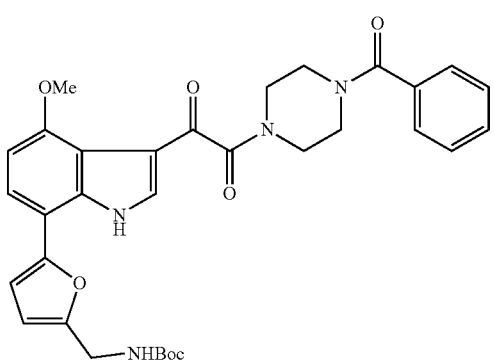 [SMILES: COc1ccc(-c2ccc(CNC(=O)OC(C)(C)C)o2)c2[nH]cc(C(=O)C(=O)N3CCN(C(=O)c4ccccc4)CC3)c12]

20

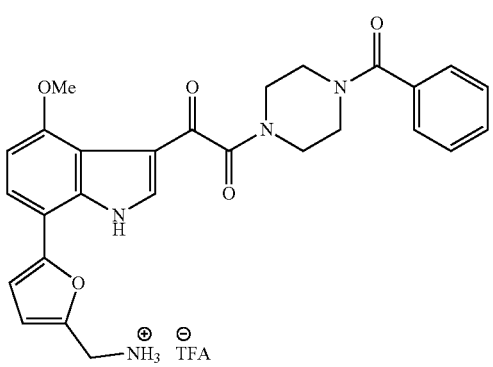 [SMILES: COc1ccc(-c2ccc(C[NH3+])o2)c2[nH]cc(C(=O)C(=O)N3CCN(C(=O)c4ccccc4)CC3)c12 ; "TFA"]

To a microwave vial (2.0-5.0 mL) containing 3 (52 mg, 0.11 mmol) in DMF/water (3.0/1.8 mL), added 5-((BOC-Amino)methyl)furan-2-boronic acid (Combi-Blocks LLC, San Diego Calif.; 37 mg, 0.154 mmol, 1.4 equiv) and NaHCO$_3$ (12.8 mg, 0.154 mmol, 1.4 equiv). Oxygen was removed from the solvent by bubbling nitrogen gas in solution for 10 min, to which Pd(PPh$_3$)$_4$ (6.3 mg, 0.0055 mmol, 5 mol %) was added. The subsequent heterogenous solution was capped and heated in microwave reactor for 12 min at 150° C. when LC/MS analysis showed reaction completion. The volatile solvents were removed by rotary evaporation and crude material was purified by flash chromatography (flash chromatography (CombiFlash Automated Chromatographer, 12 g column; gradient elution ranging from 0% methanol:dichloromethane to 15% methanol:dichloromethane was performed over 30 column volumes) to yield pure 5 as a yellow solid (52 mg, 0.088 mmol, 80%). $^1$H NMR (500 MHz, CDCl$_3$) δ 11.26 (s, 1H), 8.11 (d, J=2.6, 1H), 7.40 (bs, 5H), 6.69 (d, J=8.4, 1H), 6.52 (d, J=3.2, 1H), 6.25 (d, J=3.2, 1H), 5.20 (t, J=6.2, 1H), 4.30 (d, J=6.4, 2H), 3.93 (s, 1H), 3.91-3.33 (m, 8H), 1.45 (s, 9H). UPLC/MS: (ES+) m/z (M+H)$^+$; Rt=

To 5 (51 mg, 0.86 mmol) in dichloromethane (800 μL), added trifluoroacetic acid (250 μL), resulting in a color change from yellow to dark brown. Solution was stirred at room temperature, open to air for 1 hr when TLC (20:1 dichloromethane/methanol) showed reaction completion. Volatiles were removed by rotary evaporation, co-evaporating several times with chloroform, resulting in 6 as a yellow solid which was used without further purification. $^1$H NMR (400 MHz, CDCl$_3$) δ 7.99 (s, 1H), 7.51-7.33 (m, 6H), 6.64 (d, J=8.3, 1H), 6.54 (d, J=3.1, 1H), 6.27 (s, 1H), 3.90 (s, 3H), 3.46 (s, 8H).

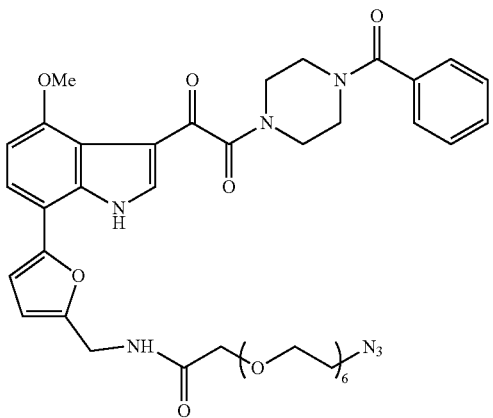

To 2 (350 mg, 0.959 mmol 1.3 equiv)) dissolved in dichloromethane (20 mL), added diisopropylethylamine (250 μL), EDC HCl (300 mg, 1.56 mmol), HOBt (250 mg, 1.63 mmol) followed by 6 (350 mg, 0.719 mmol). After 5 hrs, TLC (20:1 dichloromethane:methanol) showed reaction completion. Reaction mixture was diluted with dichloromethane (10 mL) and washed with saturated $NaHCO_3$ (3×30 mL), 2 M HCl (1×30 mL) and brine (1×30 mL) and subsequently dried over anhydrous $MgSO_4$. Solution was filtered and volatile solvents were removed by rotary evaporation. Crude yellow-orange product was purified by flash chromatography (flash chromatography (CombiFlash Automated Chromatographer, 24 g column; gradient elution ranging from 0% methanol:dichloromethane to 10% methanol:dichloromethane was performed over 30 column volumes) to yield pure 7 as a light yellow sticky solid (360 mg, 0.088 mmol, 60%). $^1$H NMR (400 MHz, $CDCl_3$) δ 11.32 (s, 1H), 8.12 (d, J=3.3, 1H), 8.07 (s, 1H), 7.38 (d, J=8.1, 6H), 6.67 (d, J=8.4, 1H), 6.51 (d, J=3.2, 1H), 6.29 (d, J=3.2, 1H), 4.52 (d, J=6.2, 2H), 4.01 (s, 2H), 3.92 (s, 3H), 3.80-3.42 (m, 28H), 3.32-3.25 (m, 2H).

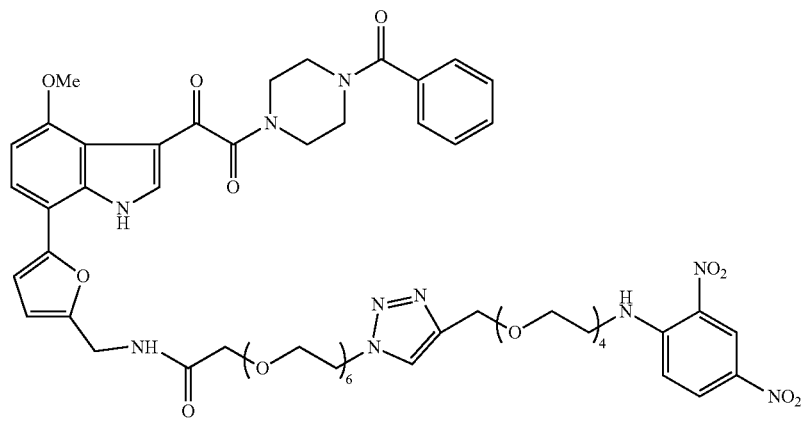

To a microwave vial containing 7 (200 mg, 0.240 mmol) in tBuOH/water (2 mL/2 mL), added alkyne 8 (100 mg, 0.261 mmol, 1.1 equiv), followed by 120 μL of 0.1M $CuSO_4$ and 240 μL of 0.1M sodium ascorbate. The reaction mixture was capped and heated to 130° C. for 30 minutes in microwave reactor when LC/MS showed reaction completion. Volatile solvents were removed by rotary evaporation and crude product was purified by HPLC (30-50% B, 36 min; Rt=27.03 min). Like fractions were combined and volatile solvents were removed by rotary evaporation, resulting in 9 as a yellow sticky solid (281 mg, 0.228 mmol, 95%). $^1$H NMR (400 MHz, $CDCl_3$) δ 11.21 (s, 1H), 9.09 (d, J=2.5, 1H), 8.77 (s, 1H), 8.18 (m, 3H), 7.74 (s, 1H), 7.52-7.34 (m, 6H), 6.92 (d, J=9.5, 1H), 6.69 (d, J=8.4, 1H), 6.54 (d, J=3.2, 1H), 6.32 (d, J=3.1, 1H), 4.65 (s, 2H), 4.58 (d, J=6.0, 2H), 4.45 (t, J=4.9, 2H), 4.08 (s, 2H), 3.94 (s, 3H), 3.83-3.28 (m, 46H). HRMS (ES+) calc'd for $C_{58}H_{74}N_{10}O_{20}$ (M+H) m/z 1231.5154. Found 12315178; for (M+Na)+, calc'd 1253.4973, found 1253.5045. Anal. HPLC Retention Time=27.89 min at 0-60% B, 36 min

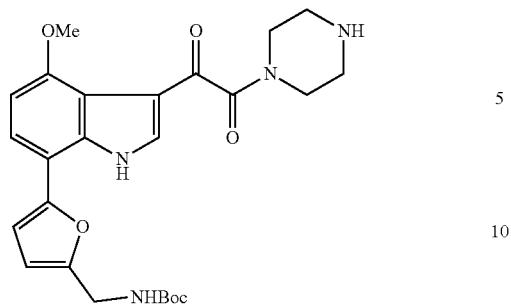
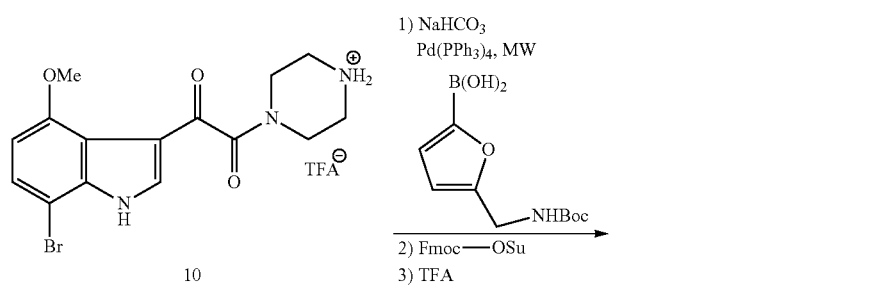
Scheme 3. Representative general route to additional analogs
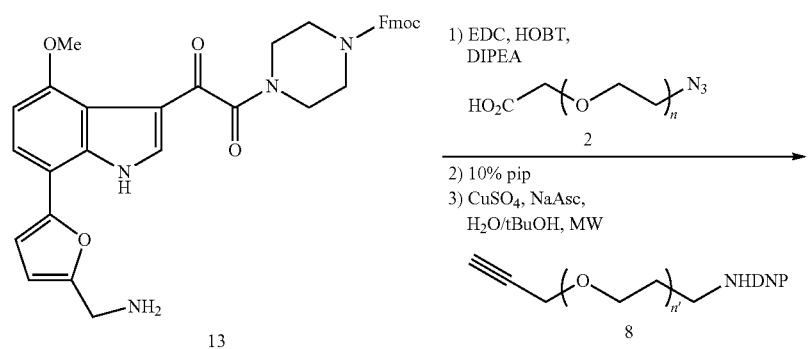
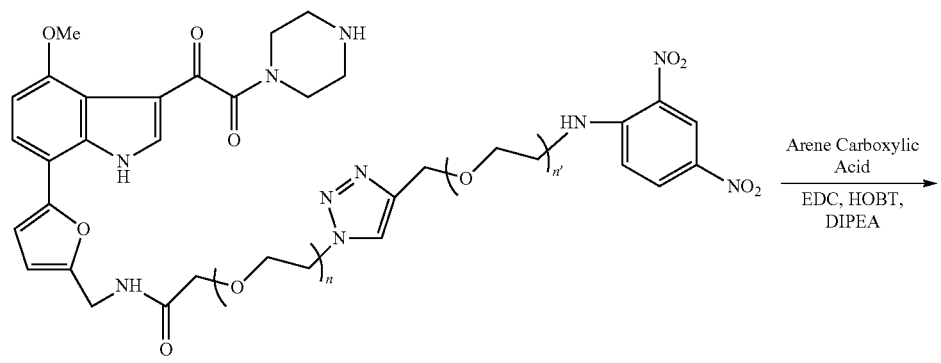

-continued

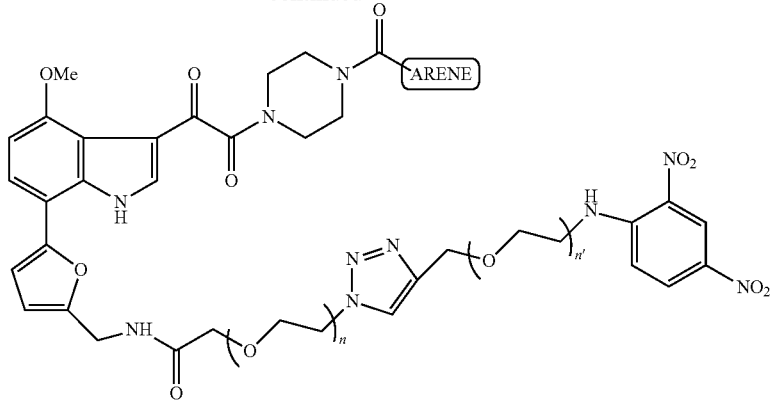

To a microwave vial (2.0-5.0 mL) containing 10 (200 mg, 0.546 mmol, available from Patent No. WO 2011046946) in DMF/water (3.0/2 mL), added 5-((BOC-Amino)methyl)furan-2-boronic acid (Combi-Blocks LLC, San Diego Calif.; 241 mg, 0.622 mmol, 1.14 equiv) and NaHCO$_3$ (50 mg, 0.595 mmol, 1.1 equiv). Oxygen was removed from the solvent by bubbling nitrogen gas in solution for 10 min, to which Pd(PPh$_3$)$_4$ (30 mg, 0.026 mmol, 5 mol %) was added. The subsequent heterogenous solution was capped and heated in microwave reactor for 15 min at 150° C. when LC/MS analysis showed reaction completion. The volatile solvents were removed by rotary evaporation and crude material was purified by flash chromatography (CombiFlash Automated Chromatographer, 24 g column; gradient elution ranging from 0% methanol:dichloromethane to 15% methanol:dichloromethane was performed over 30 column volumes) to yield pure 11 as a brown solid (225 mg, 0.467 mmol, 85%). 1H NMR (400 MHz, CDCl$_3$) δ 11.23 (s, 1H), 8.09 (s, 1H), 7.33 (d, J=8.2, 1H), 6.63 (d, J=8.2, 1H), 6.48 (d, J=3.2, 1H), 6.23 (d, J=3.2, 1H), 5.36 (s, 1H), 4.29 (s, 2H), 3.90 (brs, 5H), 3.64 (brs, 2H), 3.18 (brs, 2H), 3.09 (brs, 2H), 1.43 (s, 9H).

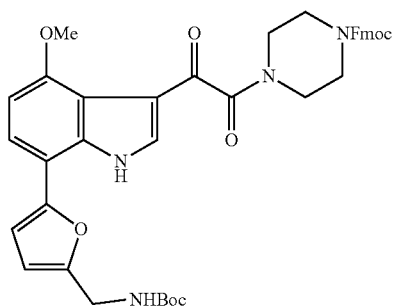

To 11 (400 mg, 0.83 mmol) dissolved in dichloromethane (20 mL), added Fmoc-OSU (560 mg, 1.66 mmol, 2 equiv) followed by diisopropylethylamine (500 μL). Resulting yellow-orange mixture was stirred at room temperature under an atmosphere of nitrogen for 12 hr when TLC (10:1 dichloromethane-methanol) showed reaction completion. The organic mixture was washed with a saturated solution of ammonium chloride (3×20 mL) and brine (1×30 mL) and then dried over anhydrous magnesium sulfate. All volatiles were removed by rotary evaporation and crude material was purified by flash chromatography (CombiFlash Automated Chromatographer, 24 g column; flushing with dichloromethane for 5 column volumes then gradient elution ranging from 0% methanol:dichloromethane to 5% methanol:dichloromethane was performed over 20 column volumes) to yield pure 12 as a yellow solid (400 mg, 0.567 mmol, 69%). 1H NMR (400 MHz, CDCl$_3$) δ 11.25 (s, 1H), 8.12 (d, J=3.1, 1H), 7.76 (brs, 2H), 7.55 (brs, 2H), 7.42 (m, 3H), 7.31 (brs, 2H), 6.70 (d, J=8.3, 1H), 6.54 (d, J=3.1, 1H), 6.26 (d, J=3.1, 1H), 5.11 (m, 1H), 4.52 (d, J=6.2, 2H), 4.32 (d, J=6.4, 2H), 4.24 (brs, 1H), 3.94 (s, 3H), 3.42 (m, 8H), 1.47 (s, 9H).

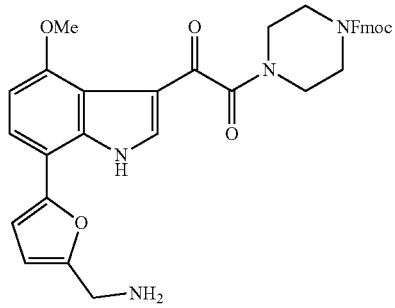

To 12 dissolved (600 mg, 0.85 mmol) in dichloromethane (15 mL), carefully added trifluoracetic acid (6 mL) and let stir at room temperature under an atmosphere of nitrogen when TLC (10:1 dichloromethane-methanol) indicated reaction completion (2 hr). All volatiles were removed by rotary evaporation and crude green residue was azeotroped with chloroform (3×10 mL) and used without further purification, yielding 13 as a TFA salt as brown solid (570 mg, 96%). $^1$H NMR (400 MHz, CDCl$_3$) δ 11.25 (s, 1H), 9.85 (s, 3H), 8.28 (s, 2H), 7.94 (s, 1H), 7.70 (s, 2H), 7.48 (s, 2H), 7.34 (s, 2H), 7.16 (d, J=7.5, 1H), 6.52 (d, J=8.1, 1H), 6.46 (s, 1H), 6.40 (s, 1H), 4.46 (d, J=4.4, 2H), 4.20 (s, 2H), 3.82 (s, 3H), 3.61-3.11 (m, 8H).

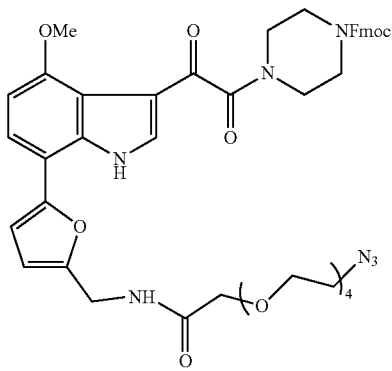

4.02 (s, 2H), 3.94 (s, 3H), 3.83-3.72 (m, 2H), 3.70-3.46 (m, 14H), 3.34-3.25 (m, 2H), 3.17-3.05 (m, 2H), 3.05-2.96 (m, 2H), 2.96-2.82 (m, 2H).

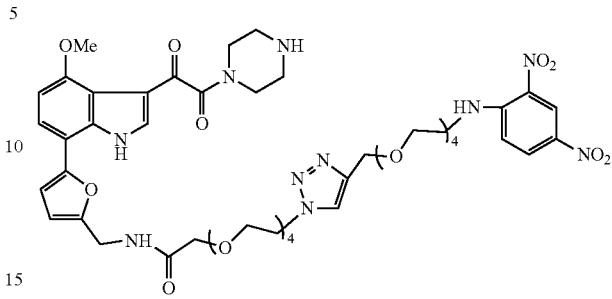

To a solution of 13 (300 mg, 0.510 mmol) in dichloromethane (25 mL), added 2 (200 mg, 0.722 mmol, 1.4 equiv), added EDC-HCl (180 mg, 3 equiv), HOBT (150 mg, 3 equiv) and diisopropylethylamine (180 μL) and let stir under an atmosphere to of nitrogen until TLC (20:1 dichloromethane-methanol) indicated reaction completion (5 hrs). The organic mixture was washed with saturated ammonium chloride (1×30 mL) and saturated sodium bicarbonate (1×30 mL) and volatiles were removed in vacuo. Resulting crude material was purified by flash chromatography (CombiFlash Automated Chromatographer, 24 g column; flushing with dichloromethane for 5 column volumes then gradient elution ranging from 0% methanol:dichloromethane to 5% methanol:dichloromethane was performed over 20 column volumes) to yield pure 14 as a yellow residue (380 mg, 0.44 mmol, 86%). $^1$H NMR (400 MHz, CDCl$_3$) δ 11.27 (s, 1H), 8.12 (d, J=3.2, 1H), 7.91 (t, J=6.1, 1H), 7.75 (brs, 2H), 7.55 (brs, 2H), 7.46-7.26 (m, 5H), 6.69 (d, J=8.3, 1H), 6.52 (d, J=3.2, 1H), 6.30 (d, J=3.2, 1H), 4.51 (m, 4H), 4.23 (brs, 1H), 4.04 (s, 2H), 3.94 (s, 3H), 3.75-3.26 (m, 24H).

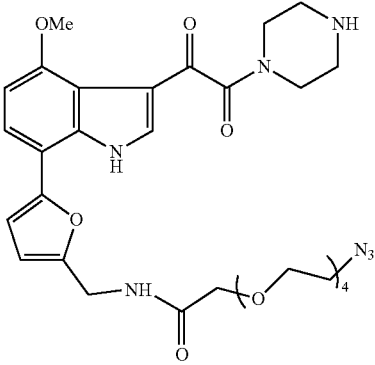

To 14 (288 mg, 0.33 mmol) in dichloromethane (2 mL), added piperadine (350 μL) and let stir under an atmosphere of nitrogen at room temperature until TLC (20:1 dichloromethane-methanol) showed reaction completion (2 hr). All volatiles were removed in vacuo and crude material was purified flash chromatography (CombiFlash Automated Chromatographer, 12 g column; gradient elution ranging from 0% methanol:dichloromethane to 20% methanol:dichloromethane was performed over 30 column volumes) to yield pure 15 as a yellow residue (170 mg, 0.265 mmol, 80%). $^1$H NMR (400 MHz, CDCl$_3$) δ 11.25 (s, 1H), 8.10 (s, 1H), 7.97 (s, 1H), 7.38 (d, J=8.3, 1H), 6.67 (d, J=8.4, 1H), 6.50 (d, J=3.2, 1H), 6.29 (d, J=3.2, 1H), 4.50 (d, J=6.2, 2H), To a microwave vial containing 15 (160 mg, 0.25 mmol) in water/tBuOH (2.3 mL/2.3 mL), added alkyne 8, 0.1M CuSO$_4$ (117 μL) in water and 0.1 M sodium ascorbate (234 μL). The reaction mixture was capped and heated to 130° C. for 30 minutes in microwave reactor when LC/MS showed reaction completion. Volatile solvents were removed by rotary evaporation and crude product was purified by flash chromatography (CombiFlash Automated Chromatographer, 12 g column; gradient elution ranging from 0% methanol:dichloromethane to 40% methanol:dichloromethane was performed over 140 column volumes) to yield 16 as a yellow residue (255 mg, 0.246 mmol, 98%). $^1$H NMR (400 MHz, CDCl$_3$) δ 11.25 (s, 1H), 9.06 (d, J=2.5, 1H), 8.75 (brs, 1H), 8.19 (d, J=9.5, 1H), 8.10 (s, 1H), 7.92 (brs, 1H), 7.66 (s, 1H), 7.37 (d, J=8.3, 1H), 6.89 (d, J=9.5, 1H), 6.67 (d, J=8.3, 1H), 6.51 (d, J=3.2, 1H), 6.28 (d, J=3.1, 1H), 4.62 (brs, 2H), 4.49 (d, J=6.1, 2H), 4.43 (t, J=5.0, 2H), 4.04 (s, 3H), 3.95 (brs, 4H), 3.91-3.41 (m, 34H), 3.13 (m, 3H).

General Synthetic Procedure for Coupling of Aryl Carboxylic Acids to (16)—See Table 1

To a 16 (10 mg, 0.01 mmol) in dichloromethane (1 mL), added arene carboxylic acid (0.018 mmol, 1.8 equiv), EDC-HCl (3.5 mg, 0.018 mmol, 1.8 equiv), HOBT (3.0 mg, 0.019 mmol, 1.9 equiv) and diisopropylethylamine (10 μL). Resulting solution was allowed to stir at room temperature under an atmosphere of nitrogen until LC/MS indicated reaction completion (5-14 hrs). Resulting solution was diluted with dichloromethane (5 mL) and then washed with a saturated solution of sodium bicarbonate (5 mL) and ammonium chloride (5 mL). The organic layer was dried over anhydrous magnesium sulfate, filtered and volatiles were removed in vacuo. Crude material was purified by HPLC.

Coupling Product (18). $^1$H NMR (400 MHz, CDCl$_3$) δ 11.28 (s, 1H), 9.07 (s, 1H), 8.76 (s, 1H), 8.20 (d, J=9.4, 1H), 8.11 (s, 1H), 7.97 (s, 1H), 7.67 (brs, 1H), 7.43-7.30 (m, 2H), 7.22-7.09 (m, 3H), 6.90 (d, J=9.5, 1H), 6.76-6.63 (m, 1H), 6.52 (brs, 1H), 6.29 (brs, 1H), 4.63 (s, 2H), 4.47 (m, 4H), 4.05 (s, 3H), 3.96-3.33 (m, 40H), 2.32 (d, J=11.8, 3H) (Note: peak broadening effect of configurational isomerism about benzoyl-piperazine amide bond).

Coupling Product (19). $^1$H NMR (400 MHz, CDCl$_3$) δ 11.20 (s, 1H), 9.06 (d, J=2.6, 1H), 8.74 (s, 1H), 8.20 (d, J=6.9, 1H), 8.12 (s, 1H), 8.00 (s, 1H), 7.67 (s, 1H), 7.39 (d, J=8.3, 1H), 7.33-7.27 (m, 2H), 7.21-7.13 (m, 1H), 6.89 (d, J=9.5, 1H), 6.68 (d, J=8.3, 1H), 6.52 (d, J=3.2, 1H), 6.30 (d, J=3.2, 1H), 4.63 (s, 2H), 4.43 (m, 2H), 4.07 (s, 2H), 3.95 (s, 3H), 3.78-3.42 (m, 38H), 2.38 (s, 3H).

Coupling Product (20). $^1$H NMR (400 MHz, CDCl$_3$) δ 11.25 (s, 1H), 9.07 (d, J=2.5, 1H), 8.75 (s, 1H), 8.20 (dd, J=2.3, 9.4, 1H), 8.12 (s, 1H), 7.99 (s, 1H), 7.67 (s, 1H), 7.39 (d, J=8.3, 1H), 7.32 (m, 1H), 7.23 (m, 2H), 6.90 (d, J=9.5, 1H), 6.68 (d, J=8.4, 1H), 6.52 (d, J=3.1, 1H), 6.29 (d, J=3.0, 1H), 4.62 (s, 2H), 4.49 (d, J=5.9, 2H), 4.44 (m, 2H), 4.06 (s, 2H), 3.95 (s, 3H), 3.89-3.49 (m, 38H), 2.38 (s, 3H).

Coupling Product (21). $^1$H NMR (400 MHz, CDCl$_3$) δ 11.21 (s, 1H), 9.05 (d, J=2.5, 1H), 8.74 (s, 1H), 8.19 (d, J=9.5, 1H), 8.11 (m, 2H), 7.63 (s, 1H), 7.36 (m, 4H), 7.24-7.18 (m, 1H), 6.88 (d, J=9.5, 1H), 6.68 (d, J=8.3, 1H), 6.52 (d, J=3.1, 1H), 6.30 (d, J=3.1, 1H), 4.59 (s, 2H), 4.52-4.24 (m, 8H), 4.08 (s, 2H), 3.94 (s, 3H), 3.85-3.33 (m, 34H), 2.68 (m, 2H), 1.24 (t, J=7.4, 3H).

Coupling Product (22). $^1$H NMR (400 MHz, CDCl$_3$) δ 11.14 (s, 1H), 9.05 (d, J=2.5, 1H), 8.74 (s, 1H), 8.24-8.09 (m, 3H), 7.67 (s, 1H), 7.37 (m, 3H), 7.29 (brs, 1H), 6.88 (d, J=9.5, 1H), 6.69 (d, J=8.4, 1H), 6.53 (d, J=3.1, 1H), 6.31 (d, J=3.1, 1H), 4.60 (s, 2H), 4.50 (d, J=5.8, 2H), 4.41 (d, J=4.7, 2H), 4.10 (brs, 2H), 3.94 (s, 3H), 3.77-3.42 (m, 38H), 3.04-2.79 (m, 1H), 1.25 (d, J=6.5, 6H).

Coupling Product (23). $^1$H NMR (500 MHz, CDCl$_3$) δ 11.08 (s, 1H), 9.05 (d, J=2.6, 1H), 8.73 (s, 1H), 8.19 (dd, J=2.6, 9.5, 1H), 8.13 (brs, 2H), 7.92 (m, 4H), 7.71 (s, 1H), 7.57 (s, 2H), 7.49 (d, J=8.1, 1H), 7.40 (d, J=8.3, 1H), 6.88 (d, J=9.5, 1H), 6.70 (d, J=8.1, 1H), 6.54 (d, J=3.1, 1H), 6.33 (d, J=3.2, 1H), 4.63 (s, 2H), 4.52 (s, 2H), 4.42 (s, 2H), 4.11 (s, 2H), 3.95 (s, 3H), 3.77 (d, J=5.1, 4H), 3.74-3.45 (m, 34H).

Coupling Product (24). $^1$H NMR (500 MHz, CDCl$_3$) δ 11.27 (s, 1H), 9.07 (d, J=2.7, 1H), 8.75 (s, 1H), 8.20 (dd, J=2.6, 9.5, 1H), 8.12 (d, J=3.2, 1H), 7.91 (s, 1H), 7.66 (s, 1H), 7.39 (d, J=8.3, 1H), 7.37-7.32 (m, 1H), 7.24 (d, J=1.4, 1H), 7.02 (d, J=8.2, 1H), 6.88 (m, 2H), 6.69 (d, J=8.4, 1H), 6.52 (d, J=3.3, 1H), 6.29 (d, J=3.2, 1H), 4.61 (s, 2H), 4.49 (d, J=6.1, 2H), 4.43 (m. 2H), 4.06 (s, 3H), 3.95-3.50 (m. 40H), 2.01 (s, 1H).

Coupling Product (25). $^1$H NMR (500 MHz, CDCl$_3$) δ 11.22 (s, 1H), 9.06 (d, J=2.6, 1H), 8.74 (s, 1H), 8.19 (d, J=9.5, 1H), 8.08 (d, J=3.3, 1H), 8.03-7.89 (brs, 1H), 7.70-7.49 (m, 1H), 7.39 (d, J=8.3, 1H), 7.25-7.2 (m, 1H), 6.91-6.87 (m, 3H), 6.68 (d, J=8.4, 1H), 6.53 (d, J=3.3, 1H), 6.31 (d, J=3.2, 1H), 4.57 (s, 2H), 4.49 (d, J=6.2, 2H), 4.45-4.25 (m, 2H), 4.07 (s, 2H), 3.94 (s, 3H), 3.83-3.39 (m, 38H), 2.01 (s, 1H).

Coupling Product (26). $^1$H NMR (400 MHz, CDCl$_3$) δ 11.17 (s, 1H), 9.03 (d, J=2.4, 1H), 8.73 (s, 1H), 8.17 (d, J=9.5, 1H), 8.09 (brs, 2H), 7.63 (s, 1H), 7.38 (d, J=8.3, 1H), 7.31-7.27 (m, 1H), 6.88-6.82 (m, 3H), 6.68 (d, J=8.3, 1H), 6.52 (d, J=2.9, 1H), 6.31 (d, J=2.8, 1H), 4.57 (s, 2H), 4.49 (d, J=4.9, 2H), 4.44-4.22 (m, 2H), 4.08 (s, 2H), 3.93 (s, 3H), 3.83-3.43 (m, 38H).

Coupling Product (27). $^1$H NMR (400 MHz, CDCl$_3$) δ 11.18 (s, 1H), 8.97 (d, J=2.3, 1H), 8.69 (s, 1H), 8.12 (d, J=9.5, 1H), 8.00 (m, 2H), 7.64 (brs, 1H), 7.33 (d, J=7.6, 1H), 6.83 (d, J=9.6, 1H), 6.62 (d, J=8.0, 1H), 6.50 (brs, 1H), 6.47-6.31 (m, 3H), 6.28 (brs, 1H), 4.57 (brs, 2H), 4.48 (brs, 2H), 4.43-4.31 (m, 2H), 4.04 (brs, 2H), 3.88 (s, 3H), 3.79-3.35 (m, 38H).

Coupling Product (28). $^1$H NMR (400 MHz, CDCl$_3$) δ 11.23 (s, 1H), 9.06 (s, 1H), 8.75 (s, 1H), 8.19 (d, J=9.5, 1H), 8.11 (brs, 2H), 7.60 (s, 1H), 7.40 (m, 5H), 6.89 (d, J=9.5, 1H), 6.68 (d, J=8.4, 1H), 6.52 (s, 1H), 6.30 (s, 1H), 4.74 (s, 2H), 4.57 (s, 2H), 4.49 (s, 2H), 4.40 (s, 2H), 4.09 (s, 2H), 3.95 (s, 3H), 3.86-3.30 (m, 38H), 1.25 (s, 1H).

Coupling Product (29). $^1$H NMR (400 MHz, CDCl$_3$) δ 11.23 (s, 1H), 9.06 (s, 1H), 8.75 (s, 1H), 8.70-8.49 (m, 1H), 8.20 (d, J=9.2, 1H), 8.13 (brs, 1H), 8.03 (brs, 1H), 7.88 (brs, 1H), 7.71 (brs, 1H), 7.63 (brs, 1H), 7.38 (m, 2H), 6.89 (d, J=9.5, 1H), 6.68 (brs, 1H), 6.52 (brs, 1H), 6.30 (brs, 1H), 4.59 (brs, 2H), 4.48 (brs, 2H), 4.41 (brs, 2H), 4.08 (brs, 2H), 3.95 (s, 3H), 3.92-3.12 (m, 38H), 2.00 (s, 3H).

Coupling Product (30). $^1$H NMR (400 MHz, CDCl$_3$) δ 11.28 (s, 1H), 9.03 (d, J=2.6, 1H), 8.73 (m, 3H), 8.16 (m, 2H), 8.08 (s, 1H), 8.01 (m, 1H), 7.60 (brs, 1H), 7.50 (s, 1H), 7.36 (d, J=8.3, 1H), 6.86 (d, J=9.5, 1H), 6.67 (d, J=8.4, 1H), 6.50 (d, J=3.3, 1H), 6.28 (d, J=3.3, 1H), 4.53-4.42 (m. 4H), 4.35 (brs, 2H), 4.09 (brs, 2H), 3.94 (s, 3H), 3.79-3.39 (m. 38H).

Coupling Product (31). 1H NMR (400 MHz, CDCl$_3$) δ 11.20 (s, 1H), 9.01 (s, 1H), 8.90 (s, 2H), 8.73 (s, 1H), 8.17 (s, 2H), 8.09 (s, 1H), 7.70 (s, 2H), 7.54 (s, 1H), 7.38 (s, 1H), 6.86 (brs, 1H), 6.69 (brs, 1H), 6.52 (brs, 1H), 6.30 (brs, 1H), 4.50 (m, 4H), 4.38 (brs, 2H), 4.11 (brs, 2H), 3.99-3.46 (m, 41H).

TABLE 1

Various synthesized compounds through general method as described from corresponding commercially available arene carboxylic acid. All activities are in μM.

|     | 9 | 18 (Me, ortho) | 19 (Me, meta) | 20 (Me, para) | 21 (Et, para) | 22 (iPr, para) | 23 (naphthyl) |
|-----|------|------|------|-------|-------|-------|------|
| CD4 | 0.29 | 5.14 | 1.36 | 0.447 | 0.469 | 0.953 | 5.24 |
| MT-2| 0.01 | ~25  | ~0.6 | 0.025 | ~0.6  | N/A   | ~5.0 |

|     | 24 (o-OH) | 25 (m-OH) | 26 (p-OH) | 27 (3,5-diOH) | 28 (p-CH$_2$OH) | 29 (2-pyridyl) | 30 (3-pyridyl) | 31 (4-pyridyl) |
|-----|-------|-------|--------|-------|-------|------|-----|-----|
| CD4 | 0.49  | 0.20  | 0.239  | 0.745 | 0.422 | 0.62 | 3.7 | 4.7 |
| MT-2| 0.2   | 0.09  | 0.09   | 0.23  | ~1.0  | 0.048| 1.3 | 9.3 |

SUMMARY

The present invention meets the strategic need for a new treatment for HIV infection by providing bifunctional small molecules generally referred to as ARM-HI's which function through orthogonal pathways—both by inhibition the gp120-CD4 interaction, and by recruiting anti-DNP antibodies to gp120-expressing cells—in preventing the cell infection and spread of HIV. It is shown that: ARM-HI's according to the present invention exhibit substantially greater activity than ARM-H compounds previously published.

The present antiviral approach has distinct advantages over other small-molecule, protein, and vaccine-based anti-HIV strategies.

Although the human immune response has been demonstrated to generate neutralizing anti-gp120 antibodies around which the virus does not effectively mutate, vaccine-based approaches toward inducing such antibodies in human hosts have not yet proven successful. In theory, although the HIV virus mutates extremely rapidly in human hosts, since it must retain CD4-binding activity in order to remain infectious, antibody-recruiting small molecules that mimic the CD4 recognition motif such as the ARM-HI's of the invention have the hope of serving the same functional role as neutralizing anti-gp120 antibodies. Furthermore, as small molecules, these materials likely possess substantial advantages over protein-based therapeutics including low propensity for immunogenicity, high metabolic stability, ready large-scale production, and relatively low cost.

The evidence suggests that a cellular immune response is necessary for viral inactivation in vivo, and the bifunctional small molecules of the invention have been shown to directly target gp120-expressing particles to macrophages and neutophils.

This approach to antiviral therapy is also ideal as a prophylactic, as the bifunctional compound are not be expected to have any significant adverse side effects, being only active when virus is present.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. Any inconsistency between the material incorporated by reference and the material set for in the specification as originally filed shall be resolved in favor of the specification as originally filed. The foregoing detailed description and examples have been given for clarity of understanding only. No unnecessary limitations are to be understood therefrom. The invention is not limited to the exact details shown and described, for variations obvious to one skilled in the art will be included within the invention defined by the following claims.

All headings are for the convenience of the reader and should not be used to limit the meaning of the text that follows the heading, unless so specified.

The invention claimed is:

1. A compound according to the chemical structure:

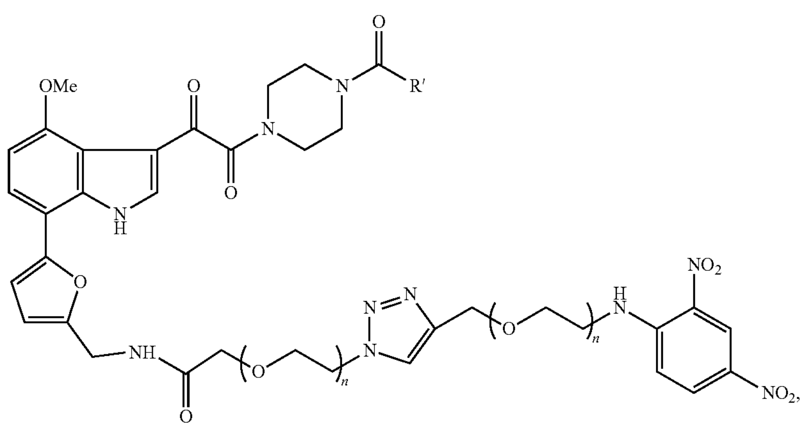

Wherein each n is independently 0, 1, 2, 3, 4, 5 or 6; and R' is phenyl, o-toluyl, m-toluyl, p-toluyl, p-ethylphenyl, p-isopropylphenyl, 2-naphthyl, o-hydroxyphenyl, m-hydroxyphenyl, p-hydroxyphenyl, 3,5-dihydroxyphenyl, p-hydroxymethylphenyl, 2-pyridyl, 3-pyridyl or 4-pyridyl, or a pharmaceutically acceptable salt thereof.

2. The compound according to claim 1 wherein each n is 3, 4, 5 or 6 and R' is phenyl, p-toluyl, p-ethylphenyl, m-hydroxyphenyl, p-hydroxyphenyl, 3,5-dihydroxyphenyl, p-hydroxymethylphenyl or 2-pyridyl, or a pharmaceutically acceptable salt thereof.

3. The compound according to claim 1, wherein each n is 3, 4, 5 or 6 and R' is phenyl, p-toluyl, p-ethylphenyl, o-hydroxyphenyl, m-hydroxyphenyl, p-hydroxyphenyl, 3,5-dihydroxyphenyl, p-hydroxymethylphenyl or 2-pyridyl, or a pharmaceutically acceptable salt thereof.

4. The compound according to claim 3 wherein each n is 4 and R' is phenyl, p-toluyl, p-ethylphenyl, o-hydroxyphenyl, m-hydroxyphenyl, p-hydroxyphenyl, 3,5-dihydroxyphenyl, p-hydroxymethylphenyl or 2-pyridyl, or a pharmaceutically acceptable salt thereof.

5. The compound according to claim 1 wherein R' is phenyl, o-toluyl, m-toluyl or p-toluyl.

6. The compound according to claim 5 wherein R' is phenyl, m-toluyl or p-toluyl.

7. The compound according to claim 1 wherein n is 3, 4, 5 or 6 and R' is phenyl, m-toluyl or p-toluyl.

8. The compound according to claim 4 wherein R' is phenyl or p-toluyl.

9. The compound according to claim 7 wherein R' is phenyl or p-toluyl.

10. The compound according to 7 wherein R' is phenyl.

11. The compound according to claim 7 wherein n is 4, 5 or 6 and R' is phenyl.

12. A pharmaceutical composition comprising an effective amount of a compound according to claim 1 in combination with a pharmaceutically acceptable carrier, additive or excipient.

13. The composition according to claim 12 further comprising an additional anti-HIV agent.

14. The composition according to claim 13 wherein said additional anti-HIV agent is selected from the group consisting of nucleoside reverse transcriptase inhibitors (NRTI), non-nucleoside reverse transcriptase inhibitors (NNRTI), reverse transcriptase inhibitors, protease inhibitors and mixtures thereof.

15. The composition according to claim 13 wherein said additional anti-HIV agent is selected from the group consisting of lamivudine, zidovudine, (−)-FTC, didanosine, zalcitabine, abacavir, tenofovir, D-D4FC (reverset), stavudine, racivir, L-FddC, L-FD4C, nevirapine, delavirdine, efavirenz, saquinavir, saquinavir mesylate, ritonavir, indinavir, nelfinavir, amprenavir, enfuvirtide, lopinavir and mixtures thereof.

16. The composition according to claim 12 in oral dosage form.

17. The composition according to claim 12 in parenteral dosage form.

18. The composition according to claim 12 in intravenous dosage form.

19. A method of treating an HIV infection in a patient in need comprising administering to said patient an effective amount of a composition according to claim 12.

20. A method of treating an HIV infection in a patient in need comprising administering to said patient an effective amount of a composition according to claim 13.

* * * * *